US012577320B2

(12) United States Patent
Fang et al.

(10) Patent No.: US 12,577,320 B2
(45) Date of Patent: Mar. 17, 2026

(54) ANTI-CLAUDIN 18.2 ANTIBODY AND ANTIBODY-DRUG CONJUGATE THEREOF

(71) Applicant: REMEGEN CO., LTD., Yantai (CN)

(72) Inventors: Jianmin Fang, Yantai (CN); Yuanhao Li, Yantai (CN); Marie M. Zhu, Yantai (CN); Jing Jiang, Yantai (CN); Yuelei Shen, Yantai (CN); Shenjun Li, Yantai (CN); Wenting Luo, Yantai (CN); Xiaoping Zhang, Yantai (CN); Lili Wang, Yantai (CN); Ling Wang, Yantai (CN); Qinbin Zhang, Yantai (CN); Fang Yang, Yantai (CN)

(73) Assignee: REMEGEN CO., LTD., Yantai (CN)

( * ) Notice: Subject to any disclaimer, the term of this patent is extended or adjusted under 35 U.S.C. 154(b) by 583 days.

(21) Appl. No.: 18/016,352

(22) PCT Filed: May 7, 2022

(86) PCT No.: PCT/CN2022/091353

§ 371 (c)(1),
(2) Date: Jan. 15, 2023

(87) PCT Pub. No.: WO2022/237666

PCT Pub. Date: Nov. 17, 2022

(65) Prior Publication Data

US 2023/0272109 A1 Aug. 31, 2023

(30) Foreign Application Priority Data

May 8, 2021 (CN) ........................ 202110502421.4

(51) Int. Cl.

| | |
|---|---|
| ***C07K 16/30*** | (2006.01) |
| ***A61K 31/351*** | (2006.01) |
| ***A61K 31/381*** | (2006.01) |
| ***A61K 31/403*** | (2006.01) |
| ***A61K 31/55*** | (2006.01) |
| ***A61K 39/395*** | (2006.01) |
| ***A61K 47/68*** | (2017.01) |
| ***A61P 35/00*** | (2006.01) |
| ***C07K 16/28*** | (2006.01) |
| ***C12N 15/63*** | (2006.01) |

(52) U.S. Cl.

CPC ............ *C07K 16/30* (2013.01); *A61K 31/351* (2013.01); *A61K 31/381* (2013.01); *A61K 31/403* (2013.01); *A61K 31/55* (2013.01); *A61K 47/6801* (2017.08); *A61P 35/00* (2018.01); *C12N 15/63* (2013.01)

(58) Field of Classification Search

None

See application file for complete search history.

(56) References Cited

U.S. PATENT DOCUMENTS

| | | | | |
|---|---|---|---|---|
| 10,421,817 | B1 * | 9/2019 | Hu | A61K 47/6801 |
| 11,912,763 | B2 * | 2/2024 | Liu | C07K 16/28 |
| 12,258,418 | B2 * | 3/2025 | Yin | C07K 14/7051 |
| 2019/0233511 | A1 | 8/2019 | Wang et al. | |
| 2020/0138968 | A1 | 5/2020 | Huang et al. | |
| 2021/0230272 | A1 | 7/2021 | Liu | |
| 2021/0261658 | A1 | 8/2021 | Wu et al. | |
| 2022/0072137 | A1 | 3/2022 | Huang et al. | |
| 2022/0119517 | A1 | 4/2022 | Wang et al. | |

FOREIGN PATENT DOCUMENTS

| | | | |
|---|---|---|---|
| CN | 108853514 | A | 11/2018 |
| CN | 109762067 | A | 5/2019 |
| CN | 110075315 | A | 8/2019 |
| CN | 110606891 | A | 12/2019 |
| CN | 110857322 | A | 3/2020 |
| CN | 110862454 | A | 3/2020 |
| CN | 111110862 | A | 5/2020 |
| CN | 111433188 | A | 7/2020 |
| CN | 111518214 | A | 8/2020 |
| CN | 111777681 | A | 10/2020 |
| CN | 111808194 | A | 10/2020 |
| CN | 111848809 | A | 10/2020 |
| CN | 111867630 | A | 10/2020 |
| EP | 3808376 | A1 | 4/2021 |
| EP | 3904386 | A1 | 11/2021 |
| JP | 2018513146 | A | 5/2018 |
| RU | 2678700 | C2 | 1/2019 |
| TW | 202108627 | A | 3/2021 |
| WO | 2019223579 | A1 | 11/2019 |
| WO | 2019242505 | A1 | 12/2019 |
| WO | 2020023679 | A1 | 1/2020 |

(Continued)

OTHER PUBLICATIONS

Balducci L (2016) Seminars Oncology Nursing, 32: 314-324.*

(Continued)

*Primary Examiner* — Ilia I Ouspenski

(74) *Attorney, Agent, or Firm* — Kilpatrick Townsend & Stockton LLP

(57) ABSTRACT

Provided are an antibody targeting Claudin 18.2, an antibody-drug conjugate, and use thereof in treatment of cancer. Also provided are a nucleotide encoding the Claudin 18.2 antibody, a polynucleotide combination, an expression vector, an expression vector combination, a pharmaceutical composition comprising the Caudill 18.2 antibody and the antibody-drug conjugate, and an application thereof in preparation of a medication for treatment or prevention of cancer.

32 Claims, 5 Drawing Sheets

Specification includes a Sequence Listing.

(56) References Cited

FOREIGN PATENT DOCUMENTS

| | | | |
|---|---|---|---|
| WO | 2020135201 | A1 | 7/2020 |
| WO | 2020135674 | A1 | 7/2020 |
| WO | 2020147321 | A1 | 7/2020 |
| WO | 2020228806 | A1 | 11/2020 |
| WO | 2021011885 | A1 | 1/2021 |

OTHER PUBLICATIONS

The extended European search report received in the counterpart European Application 22806632.0, mailed on Feb. 17, 2025.

Taiwan Patent Office, First Office Action Issued in Application No. 111117333, Jun. 5, 2023, 14 pages.

Russian Patent Office, first office action Issued in Application No. 2023100251, Aug. 15, 2023, 24 pages.

Mengchang Wang et al.,"Silence of MCL-1 upstream signaling by shRNA abrogates multiple myeloma growth", Experimental Hematology & Oncology, 2014, total 7 pages.

Beatriz Domingues et al. "Melanoma treatment in review" ImmunoTargets and therapy, 2018, total 15 pages.

Peter B. Drinks, "Brain Tumor Stem Cells: Bringing Order to the Chaos of Brain Cancer". Journal of Clinical Oncology, vol. 26, No. 17, Jun. 10, 2008, total 9 pages.

Miguel López-Lázaro, "The migration ability of stem cells can explain the existence of cancer of unknown primary site. Rethinking metastasis", Oncoscience, 2015, vol. 2, No. 5, total 9 pages.

Andrew A. Pakula et al.,"Genetic analysis of protein stability and function", Annual review of genetics, 1989, vol. 23, total 22 pages.

Dan Lu et.al., "Acquired antagonistic activity of a bispecific diabody directed against two different epitopes on vascular endothelial growth factor receptor 2", Journal of Immunological Methods, 1999, v.230, total 13 pages.

B.Tran and M.A.Rosenthal, Survival comparison between glioblastoma multiforme and other incurable cancers, Journal of Clinical Neuroscience, 2010, vol. 17, Is. 4, total 5 pages.

ON Solopova, V.A. Misyurin, Bispecific Antibodies in Clinic Practice and Clinical Trials(literature review), Clinical Oncohematology. 2019, total 20 pages.

Gunzel D. Claudins: vital partners in transcellular and paracellular transport coupling [J]. Pflugers Arch, 2017, 469 (1):35-44.

Colpitts CC, Baumert TF. Claudins in viral infection: from entry to spread [J]. Pflugers Arch, 2017, 469(1):27-34.

Hayashi D, Tamura A, Tanaka H, et al. Deficiency of claudin-18 causes paracellular H+ leakage, up-regulation of interleukin-1β, and atrophic gastritis in mice [J]. Gastroenterology, 2012, 142(2):292-304.

Li G, Flodby P, Luo J, et al. Knockout mice reveal key roles for claudin 18 in alveolar barrier properties and fluid homeostasis [J]. Am J Respir Cell Mol Biol, 2014, 51(2):210-222.

Kumar V, Soni P, Garg M, et al. Emerging Therapies in the Managment of Advanced-Stage Gastric Cancer [J]. Front Pharmacol, 2018, 9:404.

Woll S, Schlitter AM, Dhaene K , et al. Claudin 18.2 is a target for IMAB362 antibody in pancreatic neoplasms [J]. Int J Cancer, 2014, 134(3):731-739.

Jiang H, Shi Z, Wang P, et al. Claudin 18.2-Specific Chimeric Antigen Receptor Engineered T Cells for the Treatment of Gastric Cancer [J]. J Natl Cancer Inst, 2018, 111(4):1-10.

Japanese Patent Office, Office Action Issued in Application No. 2023-532228, Apr. 23, 2024, 11 pages.

* cited by examiner

```
                         SEQUENCE LISTING


<160> NUMBER OF SEQ ID NOS: 34

<210> SEQ ID NO 1
<211> LENGTH: 119
<212> TYPE: PRT
<213> ORGANISM: Artificial sequence
<220> FEATURE:
<223> OTHER INFORMATION: Heavy chain variable region

<400> SEQUENCE: 1

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Met
        35                  40                  45

Gly Leu Ile Asn Pro Gly Ser Gly Gly Thr Asn Tyr Asn Glu Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Tyr Gly Asn Ser Phe Ala Tyr Trp Gly Gln Gly
            100                 105                 110

Thr Leu Val Thr Val Ser Ser
        115


<210> SEQ ID NO 2
<211> LENGTH: 113
<212> TYPE: PRT
<213> ORGANISM: Artificial sequence
<220> FEATURE:
<223> OTHER INFORMATION: Light chain variable region

<400> SEQUENCE: 2

Asp Ile Val Met Thr Gln Ser Pro Leu Ser Leu Pro Val Thr Pro Gly
1               5                   10                  15

Glu Pro Ala Ser Ile Ser Cys Lys Ser Ser Gln Ser Leu Leu Asn Ser
            20                  25                  30

Gly Asn Gln Lys Asn Tyr Leu Thr Trp Tyr Leu Gln Lys Pro Gly Gln
        35                  40                  45

Ser Pro Gln Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Lys
65                  70                  75                  80
```

-continued

```
Ile Ser Arg Val Glu Ala Glu Asp Val Gly Val Tyr Tyr Cys Gln Asn
                85                  90                  95

Ala Tyr Tyr Tyr Pro Tyr Thr Phe Gly Gly Gly Thr Lys Val Glu Ile
            100                 105                 110

Lys


<210> SEQ ID NO 3
<211> LENGTH: 7
<212> TYPE: PRT
<213> ORGANISM: Artificial sequence
<220> FEATURE:
<223> OTHER INFORMATION: CDR of heavy chain

<400> SEQUENCE: 3

Gly Tyr Ala Phe Thr Asn Tyr
1               5


<210> SEQ ID NO 4
<211> LENGTH: 10
<212> TYPE: PRT
<213> ORGANISM: Artificial sequence
<220> FEATURE:
<223> OTHER INFORMATION: CDR of heavy chain

<400> SEQUENCE: 4

Gly Tyr Ala Phe Thr Asn Tyr Leu Ile Glu
1               5                   10


<210> SEQ ID NO 5
<211> LENGTH: 5
<212> TYPE: PRT
<213> ORGANISM: Artificial sequence
<220> FEATURE:
<223> OTHER INFORMATION: CDR of heavy chain

<400> SEQUENCE: 5

Asn Tyr Leu Ile Glu
1               5


<210> SEQ ID NO 6
<211> LENGTH: 6
<212> TYPE: PRT
<213> ORGANISM: Artificial sequence
<220> FEATURE:
<223> OTHER INFORMATION: CDR of heavy chain

<400> SEQUENCE: 6

Thr Asn Tyr Leu Ile Glu
1               5


<210> SEQ ID NO 7
<211> LENGTH: 8
<212> TYPE: PRT
<213> ORGANISM: Artificial sequence
<220> FEATURE:
<223> OTHER INFORMATION: CDR of heavy chain

<400> SEQUENCE: 7

Gly Tyr Ala Phe Thr Asn Tyr Leu
1               5


<210> SEQ ID NO 8
<211> LENGTH: 6
<212> TYPE: PRT
<213> ORGANISM: Artificial sequence
<220> FEATURE:
```

<223> OTHER INFORMATION: CDR of heavy chain

<400> SEQUENCE: 8

Asn Pro Gly Ser Gly Gly
1 5

<210> SEQ ID NO 9
<211> LENGTH: 10
<212> TYPE: PRT
<213> ORGANISM: Artificial sequence
<220> FEATURE:
<223> OTHER INFORMATION: CDR of heavy chain

<400> SEQUENCE: 9

Leu Ile Asn Pro Gly Ser Gly Gly Thr Asn
1 5 10

<210> SEQ ID NO 10
<211> LENGTH: 17
<212> TYPE: PRT
<213> ORGANISM: Artificial sequence
<220> FEATURE:
<223> OTHER INFORMATION: CDR of heavy chain

<400> SEQUENCE: 10

Leu Ile Asn Pro Gly Ser Gly Gly Thr Asn Tyr Asn Glu Lys Phe Lys
1 5 10 15

Gly

<210> SEQ ID NO 11
<211> LENGTH: 13
<212> TYPE: PRT
<213> ORGANISM: Artificial sequence
<220> FEATURE:
<223> OTHER INFORMATION: CDR of heavy chain

<400> SEQUENCE: 11

Trp Met Gly Leu Ile Asn Pro Gly Ser Gly Gly Thr Asn
1 5 10

<210> SEQ ID NO 12
<211> LENGTH: 8
<212> TYPE: PRT
<213> ORGANISM: Artificial sequence
<220> FEATURE:
<223> OTHER INFORMATION: CDR of heavy chain

<400> SEQUENCE: 12

Ile Asn Pro Gly Ser Gly Gly Thr
1 5

<210> SEQ ID NO 13
<211> LENGTH: 10
<212> TYPE: PRT
<213> ORGANISM: Artificial sequence
<220> FEATURE:
<223> OTHER INFORMATION: CDR of heavy chain

<400> SEQUENCE: 13

Gly Gly Tyr Tyr Gly Asn Ser Phe Ala Tyr
1 5 10

<210> SEQ ID NO 14
<211> LENGTH: 10
<212> TYPE: PRT
<213> ORGANISM: Artificial sequence -continued
<220> FEATURE:
<223> OTHER INFORMATION: CDR of heavy chain

<400> SEQUENCE: 14

Gly Gly Tyr Tyr Gly Asn Ser Phe Ala Tyr
1 5 10

<210> SEQ ID NO 15
<211> LENGTH: 10
<212> TYPE: PRT
<213> ORGANISM: Artificial sequence
<220> FEATURE:
<223> OTHER INFORMATION: CDR of heavy chain

<400> SEQUENCE: 15

Gly Gly Tyr Tyr Gly Asn Ser Phe Ala Tyr
1 5 10

<210> SEQ ID NO 16
<211> LENGTH: 11
<212> TYPE: PRT
<213> ORGANISM: Artificial sequence
<220> FEATURE:
<223> OTHER INFORMATION: CDR of heavy chain

<400> SEQUENCE: 16

Ala Arg Gly Gly Tyr Tyr Gly Asn Ser Phe Ala
1 5 10

<210> SEQ ID NO 17
<211> LENGTH: 12
<212> TYPE: PRT
<213> ORGANISM: Artificial sequence
<220> FEATURE:
<223> OTHER INFORMATION: CDR of heavy chain

<400> SEQUENCE: 17

Ala Arg Gly Gly Tyr Tyr Gly Asn Ser Phe Ala Tyr
1 5 10

<210> SEQ ID NO 18
<211> LENGTH: 17
<212> TYPE: PRT
<213> ORGANISM: Artificial sequence
<220> FEATURE:
<223> OTHER INFORMATION: CDR of light chain

<400> SEQUENCE: 18

Lys Ser Ser Gln Ser Leu Leu Asn Ser Gly Asn Gln Lys Asn Tyr Leu
1 5 10 15

Thr

<210> SEQ ID NO 19
<211> LENGTH: 17
<212> TYPE: PRT
<213> ORGANISM: Artificial sequence
<220> FEATURE:
<223> OTHER INFORMATION: CDR of light chain

<400> SEQUENCE: 19

Lys Ser Ser Gln Ser Leu Leu Asn Ser Gly Asn Gln Lys Asn Tyr Leu
1 5 10 15

Thr

<210> SEQ ID NO 20

<211> LENGTH: 17
<212> TYPE: PRT
<213> ORGANISM: Artificial sequence
<220> FEATURE:
<223> OTHER INFORMATION: CDR of light chain

<400> SEQUENCE: 20

Lys Ser Ser Gln Ser Leu Leu Asn Ser Gly Asn Gln Lys Asn Tyr Leu
1 5 10 15

Thr

<210> SEQ ID NO 21
<211> LENGTH: 13
<212> TYPE: PRT
<213> ORGANISM: Artificial sequence
<220> FEATURE:
<223> OTHER INFORMATION: CDR of light chain

<400> SEQUENCE: 21

Leu Asn Ser Gly Asn Gln Lys Asn Tyr Leu Thr Trp Tyr
1 5 10

<210> SEQ ID NO 22
<211> LENGTH: 12
<212> TYPE: PRT
<213> ORGANISM: Artificial sequence
<220> FEATURE:
<223> OTHER INFORMATION: CDR of light chain

<400> SEQUENCE: 22

Gln Ser Leu Leu Asn Ser Gly Asn Gln Lys Asn Tyr
1 5 10

<210> SEQ ID NO 23
<211> LENGTH: 7
<212> TYPE: PRT
<213> ORGANISM: Artificial sequence
<220> FEATURE:
<223> OTHER INFORMATION: CDR of light chain

<400> SEQUENCE: 23

Trp Ala Ser Thr Arg Glu Ser
1 5

<210> SEQ ID NO 24
<211> LENGTH: 7
<212> TYPE: PRT
<213> ORGANISM: Artificial sequence
<220> FEATURE:
<223> OTHER INFORMATION: CDR of light chain

<400> SEQUENCE: 24

Trp Ala Ser Thr Arg Glu Ser
1 5

<210> SEQ ID NO 25
<211> LENGTH: 7
<212> TYPE: PRT
<213> ORGANISM: Artificial sequence
<220> FEATURE:
<223> OTHER INFORMATION: CDR of light chain

<400> SEQUENCE: 25

Trp Ala Ser Thr Arg Glu Ser
1 5

-continued

<210> SEQ ID NO 26
<211> LENGTH: 10
<212> TYPE: PRT
<213> ORGANISM: Artificial sequence
<220> FEATURE:
<223> OTHER INFORMATION: CDR of light chain

<400> SEQUENCE: 26

Leu Leu Ile Tyr Trp Ala Ser Thr Arg Glu
1               5                   10

<210> SEQ ID NO 27
<211> LENGTH: 3
<212> TYPE: PRT
<213> ORGANISM: Artificial sequence
<220> FEATURE:
<223> OTHER INFORMATION: CDR of light chain

<400> SEQUENCE: 27

Trp Ala Ser
1

<210> SEQ ID NO 28
<211> LENGTH: 9
<212> TYPE: PRT
<213> ORGANISM: Artificial sequence
<220> FEATURE:
<223> OTHER INFORMATION: CDR of light chain

<400> SEQUENCE: 28

Gln Asn Ala Tyr Tyr Tyr Pro Tyr Thr
1               5

<210> SEQ ID NO 29
<211> LENGTH: 9
<212> TYPE: PRT
<213> ORGANISM: Artificial sequence
<220> FEATURE:
<223> OTHER INFORMATION: CDR of light chain

<400> SEQUENCE: 29

Gln Asn Ala Tyr Tyr Tyr Pro Tyr Thr
1               5

<210> SEQ ID NO 30
<211> LENGTH: 9
<212> TYPE: PRT
<213> ORGANISM: Artificial sequence
<220> FEATURE:
<223> OTHER INFORMATION: CDR of light chain

<400> SEQUENCE: 30

Gln Asn Ala Tyr Tyr Tyr Pro Tyr Thr
1               5

<210> SEQ ID NO 31
<211> LENGTH: 8
<212> TYPE: PRT
<213> ORGANISM: Artificial sequence
<220> FEATURE:
<223> OTHER INFORMATION: CDR of light chain

<400> SEQUENCE: 31

Gln Asn Ala Tyr Tyr Tyr Pro Tyr
1               5

<210> SEQ ID NO 32

<211> LENGTH: 9
<212> TYPE: PRT
<213> ORGANISM: Artificial sequence
<220> FEATURE:
<223> OTHER INFORMATION: CDR of light chain

<400> SEQUENCE: 32

Gln Asn Ala Tyr Tyr Tyr Pro Tyr Thr
1               5

<210> SEQ ID NO 33
<211> LENGTH: 449
<212> TYPE: PRT
<213> ORGANISM: Artificial sequence
<220> FEATURE:
<223> OTHER INFORMATION: Heavy chain

<400> SEQUENCE: 33

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Met
        35                  40                  45

Gly Leu Ile Asn Pro Gly Ser Gly Gly Thr Asn Tyr Asn Glu Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Tyr Gly Asn Ser Phe Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu 305 310 315 320

Tyr Lys Cys Lys Val Ser Asn Lys Ala Leu Pro Ala Pro Ile Glu Lys
325 330 335

Thr Ile Ser Lys Ala Lys Gly Gln Pro Arg Glu Pro Gln Val Tyr Thr
340 345 350

Leu Pro Pro Ser Arg Glu Glu Met Thr Lys Asn Gln Val Ser Leu Thr
355 360 365

Cys Leu Val Lys Gly Phe Tyr Pro Ser Asp Ile Ala Val Glu Trp Glu
370 375 380

Ser Asn Gly Gln Pro Glu Asn Asn Tyr Lys Thr Thr Pro Pro Val Leu
385 390 395 400

Asp Ser Asp Gly Ser Phe Phe Leu Tyr Ser Lys Leu Thr Val Asp Lys
405 410 415

Ser Arg Trp Gln Gln Gly Asn Val Phe Ser Cys Ser Val Met His Glu
420 425 430

Ala Leu His Asn His Tyr Thr Gln Lys Ser Leu Ser Leu Ser Pro Gly
435 440 445

Lys

<210> SEQ ID NO 34
<211> LENGTH: 220
<212> TYPE: PRT
<213> ORGANISM: Artificial sequence
<220> FEATURE:
<223> OTHER INFORMATION: Light chain

<400> SEQUENCE: 34

Asp Ile Val Met Thr Gln Ser Pro Leu Ser Leu Pro Val Thr Pro Gly
1 5 10 15

Glu Pro Ala Ser Ile Ser Cys Lys Ser Ser Gln Ser Leu Leu Asn Ser
20 25 30

Gly Asn Gln Lys Asn Tyr Leu Thr Trp Tyr Leu Gln Lys Pro Gly Gln
35 40 45

Ser Pro Gln Leu Leu Ile Tyr Trp Ala Ser Thr Arg Glu Ser Gly Val
50 55 60

Pro Asp Arg Phe Ser Gly Ser Gly Ser Gly Thr Asp Phe Thr Leu Lys
65 70 75 80

Ile Ser Arg Val Glu Ala Glu Asp Val Gly Val Tyr Tyr Cys Gln Asn
85 90 95

Ala Tyr Tyr Tyr Pro Tyr Thr Phe Gly Gly Gly Thr Lys Val Glu Ile
100 105 110

Lys Arg Thr Val Ala Ala Pro Ser Val Phe Ile Phe Pro Pro Ser Asp
115 120 125

Glu Gln Leu Lys Ser Gly Thr Ala Ser Val Val Cys Leu Leu Asn Asn
130 135 140

Phe Tyr Pro Arg Glu Ala Lys Val Gln Trp Lys Val Asp Asn Ala Leu
145 150 155 160

Gln Ser Gly Asn Ser Gln Glu Ser Val Thr Glu Gln Asp Ser Lys Asp
165 170 175

Ser Thr Tyr Ser Leu Ser Ser Thr Leu Thr Leu Ser Lys Ala Asp Tyr
180 185 190

-continued

```
Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

ANTI-CLAUDIN 18.2 ANTIBODY AND ANTIBODY-DRUG CONJUGATE THEREOF

CROSS-REFERENCE OF RELATED APPLICATIONS

The present application is a national phase of International Application No. PCT/CN2022/091353, titled "ANTI-CLAUDIN 18.2 ANTIBODY AND ANTIBODY-DRUG CONJUGATE THEREOF", filed on May 7, 2022, which claims priority to Chinese Patent Application No. CN202110502421.4, titled "ANTI-CLAUDIN 18.2 ANTIBODY AND ANTIBODY-DRUG CONJUGATE THEREOF", filed on May 8, 2021 with the China National Intellectual Property Administration, which are incorporated herein by reference in their entireties.

FIELD

The present disclosure relates to the field of biomedicine, and in particular relates to an anti-Claudin 18.2 antibody and antibody-drug conjugate thereof, and the present disclosure also relates to use of the above-mentioned antibody and antibody-drug conjugate thereof.

BACKGROUND

In recent years, the overall incidence of malignant tumors in the world has shown a continuous upward trend, seriously threatening human health and survival. At present, the clinical treatment of malignant tumors mainly includes surgery, chemotherapy and radiotherapy, which fail to achieve satisfactory curative effect though. Antibody-drug conjugate (ADC) refers to a class of biological drugs formed by linking a biologically active drug to an antibody via a chemical linker. For the past few years, multiple antibody-drug conjugates have made breakthroughs in the treatment of malignant tumors, making them an emerging treatment method after surgery, chemotherapy and radiotherapy. However, as of March 2021, only 11 antibody-drug conjugates have been approved in the world (10 approved by the US FDA and one approved by the Japanese PMDA) with only a few approved indications, which are far from meeting the current clinical needs of patients with malignant tumors.

TABLE 1

Marketed antibody-drug conjugates

| Generic name | Companies | Target | Time to market |
|---|---|---|---|
| Brentuximab vedotin | Seattle, Takeda | CD30 | 2011 |
| Ado-trastuzumab emtansine | Genentech | Her2 | 2013 |
| Inotuzumab ozogamicin | Pfizer | CD22 | 2017 |
| Gemtuzumab ozogamicin | Pfizer | CD33 | 2017 |
| Moxetumomab pasudotox-tdfk | AstraZeneca | CD22 | 2018 |
| Enfortumab vedotin-ejfv | Seattle/Astellas | Nectin-4 | 2019 |
| Polatuzumab vedotin-piiq | Genentech | CD79b | 2019 |
| Fam-trastuzumab deruxtecan-nxki | AstraZeneca/ Daiichi Sankyo | Her2 | 2019 |
| Sacituzumab govitecan-hziy | Immunomedics | Trop2 | 2020 |
| Belantamab mafodotin | Glaxosmithkline (Ireland) Ltd | BCMA | 2020 |
| Cetuximab sarotalocan | Rakuten Medical | EGFR | 2020 |

Note:
Mylotarg was withdrawn from the market in 2010 after being approved for marketing in 2000, and was re-approved for marketing in 2017.

Cell junction claudins (Claudins or CLDNs) are widely distributed in various epithelial tissues and are important structural components for cell tight junctions. Studies have found that CLDNs are closely related to the maintenance of osmotic pressure, barrier function and cell polarity in epithelial cells (Document 1: Gunzel D. Claudins: vital partners in transcellular and paracellular transport coupling [J]. Pflugers Arch, 2017, 469(1):35-44.), and are involved in the immune defense process against pathogens (Document 2: Colpitts C C, Baumert T F. Claudins in viral infection: from entry to spread [J]. Pflugers Arch, 2017, 469(1):27-34.). In addition, CLDNs have been confirmed to have changes in expression patterns during the occurrence and development of many tumors, and the research on targeted therapy studies using CLDN lineages as specific marker proteins has attracted extensive attention. However, although most CLDNs are widely expressed, some members such as CLDN 18 protein are often highly selectively expressed in specific tissues such as the gastrointestinal tract. The CLDN18 gene is located at 3q22.3 of human chromosome 3, and there are two options for the first exon of the gene, thus forming two different splice mutants expressing two protein isoforms, which differ in 69 amino acids at N-terminal, namely Claudin 18.1 protein and CLDN 18.2 protein (Document 3: Hayashi D, Tamura A, Tanaka H, et al. Deficiency of claudin-18 causes paracellular H+ leakage, up-regulation of interleukin-1β, and atrophic gastritis in mice [J]. Gastroenterology, 2012, 142(2):292-304.). Claudin 18.1 protein is a specific antigen selectively expressed by alveolar epithelial cells, and is only highly expressed in normal alveolar tissue and not found in other normal tissues including pancreatic duct (Document 4: Li G, Flodby P, Luo J, et al. Knockout mice reveal key roles for claudin 18 in alveolar barrier properties and fluid homeostasis [J]. Am J Respir Cell Mol Biol, 2014, 51(2):210-222.). Claudin 18.2 protein is also a highly selective marker protein, but the tissues in which it is distributed are completely different from those of Claudin 18.1 protein. The expression of Claudin 18.2 protein is highly limited in normal healthy tissues, but aberrantly activated and overexpressed in various primary malignant tumors such as gastric cancer, breast cancer, colon cancer, liver cancer, head and neck cancer, bronchial cancer, and non-small cell lung cancer, especially in malignant tumors of the digestive system, including gastric cancer (70%), pancreatic cancer (50%), esophageal cancer (30%), etc. (Document 5: Kumar V, Soni P, Garg M, et al. Emerging Therapies in the Managment of Advanced-Stage Gastric Cancer [J]. Front Pharmacol, 2018, 9:404.). Another study has shown that the CLDN 18.2 protein is not just expressed in the primary lesions but also highly expressed in the metastatic lesions, and may participate in the process of proliferation and chemotaxis of malignant tumor cells (Document 6: Woll S, Schlitter A M, Dhaene K, et al. Claudin 18.2 is a target for IMAB362 antibody in pancreatic neoplasms [J]. Int J Cancer, 2014, 134(3):731-739; Document 7: Jiang H, Shi Z, Wang P, et al. Claudin18.2-Specific Chimeric Antigen Receptor Engineered T Cells for the Treatment of Gastric Cancer [J]. J Natl Cancer Inst, 2018, 111(4):1-10.). Therefore, Claudin 18.2 is a very ideal tumor marker and target for anti-tumor drug development, especially for gastric cancer, pancreatic cancer, esophageal cancer, lung cancer, ovarian cancer, etc. However, due to its special target (the structure is highly similar to that of Claudin 18.1 with exactly the same first domain of the extracellular region), the development of Claudin 18.2 therapeutic antibody is very difficult, which is also the main reason for limiting the development of Claudin 18.2-targeted drugs.

Currently, the antibody-drug conjugates targeting Claudin 18.2 are all in the preclinical research stage, and none of them has advanced to the clinical stage. Therefore, it is urgent to develop antibody-drug conjugates targeting Claudin 18.2 to provide more clinical options.

SUMMARY

The present disclosure provides an antibody targeting Claudin 18.2, an antibody-drug conjugate and use thereof in the treatment of cancer. The present disclosure also provides a nucleotide encoding the above-mentioned Claudin 18.2 antibody, a polynucleotide combination, an expression vector and an expression vector combination, a pharmaceutical composition including the above-mentioned Claudin 18.2 antibody or antibody-drug conjugate, as well as their use in the manufacture of a medicament for treating or preventing cancer.

One embodiment of the present disclosure provides an anti-Claudin 18.2 antibody or antigen-binding fragment thereof, and the antibody or antigen-binding fragment thereof includes a heavy chain variable region and a light chain variable region. The heavy chain variable region and/or the light chain variable region has a CDR sequence identical to that of an antibody defined by the following sequence or obtained by 1-2 amino acid substitutions of the CDR of the antibody defined by the following sequence:

(1) an amino acid sequence of a heavy chain variable region as shown in SEQ ID NO: 1; and/or (2) an amino acid sequence of a light chain variable region as shown in SEQ ID NO: 2.

In one embodiment, according to different determination methods or system identifications, the complementarity determining regions (CDRs) 1-3 of the corresponding heavy chain and light chain variable regions are as shown in Table 2.

Further, the present disclosure also provides an anti-Claudin 18.2 antibody or antigen-binding fragment thereof, which in some embodiments, includes a heavy chain variable region and light chain variable region, and:

(1) for the heavy chain variable region, CDR1 has an amino acid sequence as shown in SEQ ID NO: 3, 4, 5, 6 or 7 or obtained by 1 or 2 amino acid substitutions of SEQ ID NO: 3, 4, 5, 6 or 7; CDR2 has an amino acid sequence as shown in SEQ ID NO: 8, 9, 10, 11 or 12, or obtained by 1 or 2 amino acid substitutions of SEQ ID NO: 8, 9, 10, 11 or 12; CDR3 has an amino acid sequence as shown in SEQ ID NO: 13, 14, 15, 16 or 17, or obtained by 1 or 2 amino acid substitutions of SEQ ID NO: 13, 14, 15, 16 or 17;

(2) for the light chain variable region, CDR1 has an amino acid sequence as shown in SEQ ID NO: 18, 19, 20, 21 or 22 or obtained by 1 or 2 amino acid substitutions of SEQ ID NO: 18, 19, 20, 21 or 22; CDR2 has an amino acid sequence as shown in SEQ ID NO: 23, 24, 25, 26 or 27, or obtained by 1 or 2 amino acid substitutions of SEQ ID NO: 23, 24, 25, 26 or 27; CDR3 has an amino acid sequence as shown in SEQ ID NO: 28, 29, 30, 31 or 32, or obtained by 1 or 2 amino acid substitutions of SEQ ID NO: 28, 29, 30, 31 or 32.

Further, in some embodiments, the present disclosure provides an anti-Claudin 18.2 antibody or antigen-binding fragment, and:

(1) CDRs 1-3 of the heavy chain variable region have amino acid sequences of SEQ ID NOs: 3, 8 and 13 or obtained by 1 or 2 amino acid substitutions of SEQ ID NOs: 3, 8 and 13, and/or the CDRs 1-3 of the light chain variable region have amino acid sequences of SEQ ID NOs: 18, 23 and 28 or obtained by 1 or 2 amino acid substitutions of SEQ ID NOs: 18, 23 and 28;

(2) CDRs 1-3 of the heavy chain variable region have amino acid sequences of SEQ ID NOs: 4, 9 and 14 or obtained by 1 or 2 amino acid substitutions of SEQ ID NOs: 4, 9 and 14, and/or the CDRs 1-3 of the light

TABLE 2

Amino acid sequences of CDRs 1-3 of heavy chain and light chain variable regions

| Category | System | CDR1 | CDR2 | CDR3 |
|---|---|---|---|---|
| Heavy chain | Chothia | SEQ ID NO: 3<br>GYAFTNY | SEQ ID NO: 8<br>NPGSGG | SEQ ID NO: 13<br>GGYYGNSFAY |
| | AbM | SEQ ID NO: 4<br>GYAFTNYLIE | SEQ ID NO: 9<br>LINPGSGGTN | SEQ ID NO: 14<br>GGYYGNSFAY |
| | Kabat | SEQ ID NO: 5<br>NYLIE | SEQ ID NO: 10<br>LINPGSGGTNYNEKFKG | SEQ ID NO: 15<br>GGYYGNSFAY |
| | Contact | SEQ ID NO: 6<br>TNYLIE | SEQ ID NO: 11<br>WMGLINPGSGGTN | SEQ ID NO: 16<br>ARGGYYGNSFA |
| | IMGT | SEQ ID NO: 7<br>GYAFTNYL | SEQ ID NO: 12<br>INPGSGGT | SEQ ID NO: 17<br>ARGGYYGNSFAY |
| Light chain | Chothia | SEQ ID NO: 18<br>KSSQSLLNSGNQKNYLT | SEQ ID NO: 23<br>WASTRES | SEQ ID NO: 28<br>QNAYYYPYT |
| | AbM | SEQ ID NO: 19<br>KSSQSLLNSGNQKNYLT | SEQ ID NO: 24<br>WASTRES | SEQ ID NO: 29<br>QNAYYYPYT |
| | Kabat | SEQ ID NO: 20<br>KSSQSLLNSGNQKNYLT | SEQ ID NO: 25<br>WASTRES | SEQ ID NO: 30<br>QNAYYYPYT |
| | Contact | SEQ ID NO: 21<br>LNSGNQKNYLTWY | SEQ ID NO: 26<br>LLIYWASTRE | SEQ ID NO: 31<br>QNAYYYPY |
| | IMGT | SEQ ID NO: 22<br>QSLLNSGNQKNY | SEQ ID NO: 27<br>WAS | SEQ ID NO: 32<br>QNAYYYPYT |

chain variable region have amino acid sequences of SEQ ID NOs: 19, 24 and 29 or obtained by 1 or 2 amino acid substitutions of SEQ ID NOs: 19, 24 and 29;

(3) CDRs 1-3 of the heavy chain variable region have amino acid sequences of SEQ ID NOs: 5, 10 and 15 or obtained by 1 or 2 amino acid substitutions of SEQ ID NOs: 5, 10 and 15, and/or the CDRs 1-3 of the light chain variable region have amino acid sequences of SEQ ID NOs: 20, 25 and 30 or obtained by 1 or 2 amino acid substitutions of SEQ ID NOs: 20, 25 and 30;

(4) CDRs 1-3 of the heavy chain variable region have amino acid sequences of SEQ ID NOs: 6, 11 and 16 or obtained by 1 or 2 amino acid substitutions of SEQ ID NOs: 6, 11 and 16, and/or the CDRs 1-3 of the light chain variable region have amino acid sequences of SEQ ID NOs: 21, 26 and 31 or obtained by 1 or 2 amino acid substitutions of SEQ ID NOs: 21, 26 and 31;

(5) CDRs 1-3 of the heavy chain variable region have amino acid sequences of SEQ ID NOs: 7, 12 and 17 or obtained by 1 or 2 amino acid substitutions of SEQ ID NOs: 7, 12 and 17, and/or the CDRs 1-3 of the light chain variable region have amino acid sequences of SEQ ID NOs: 22, 27 and 32 or obtained by 1 or 2 amino acid substitutions of SEQ ID NOs: 22, 27 and 32.

In some embodiments, the present disclosure provides an antibody or antigen-binding fragment thereof, including a variable region selected from the following group:

(1) a heavy chain variable region having an amino acid sequence as shown in SEQ ID NO: 1, or including the same CDRs 1-3 as in SEQ ID NO: 1 and more than 80%, 85%, 90%, 95%, 96%, 97%, 98%, or 99% identical to SEQ ID NO: 1; and/or (2) a light chain variable region having an amino acid sequence as shown in SEQ ID NO: 2, or including the same CDRs 1-3 as in SEQ ID NO: 2 and more than 80%, 85%, 90%, 95%, 96%, 97%, 98%, or 99% identical to SEQ ID NO: 2.

In one embodiment, the heavy chain variable region of the anti-Claudin 18.2 antibody of the present disclosure has an amino acid sequence as follows (SEQ ID NO: 1):

QVQLVQSGAE VKKPGASVKV SCKASGYAFT NYLIEWVRQA PGQGLEWMGL INPGSGGTNY 60 NEKFKGRVTM TRDTSTSTVY MELSSLRSED TAVYYCARGG YYGNSFAYWG QGTLVTVSS 119

In one embodiment, the light chain variable region of the anti-Claudin 18.2 antibody of the present disclosure has an amino acid sequence as follows (SEQ ID NO: 2):

DIVMTQSPLS LPVTPGEPAS ISCKSSQSLL NSGNQKNYLT WYLQKPGQSP QLLIYWASTR 60 ESGVPDRFSG SGSGTDFTLK ISRVEAEDVG VYYCQNAYYY PYTFGGGTKV EIK 113

In one embodiment, the present disclosure provides an anti-Claudin 18.2 antibody or antigen-binding fragment thereof, including: (1) a heavy chain variable region with an amino acid sequence as shown in SEQ ID NO: 1; and/or (2) a light chain variable region with an amino acid as shown in SEQ ID NO: 2.

In some embodiments, the present disclosure provides an antibody or antigen-binding fragment thereof, and: (1) the heavy chain has an amino acid sequence as shown in SEQ ID NO: 33; and/or (2) the light chain has an amino acid sequence as shown in SEQ ID NO: 34.

The antibody provided by the present disclosure may be a monoclonal antibody, Fab, Fab', Fab'-SH, F(ab')2, Fv, single chain Fv (scFv), diabody, bispecific antibody, multi-specific antibody, chimeric antibody, humanized antibody or fusion protein including an antigen-binding fragment of an antibody; may be the antibody is a humanized monoclonal antibody.

The antibody provided by the present disclosure further includes a human or murine constant region; may be the constant region is selected from the group consisting of IgG1, IgG2, IgG3, and IgG4.

The present disclosure also provides an antibody-drug conjugate including the above-mentioned antibody or antigen-binding fragment thereof.

Further, the antibody-drug conjugate has a structure represented by formula (I):

Ab-L-D (I)

and:

Ab is the above-mentioned antibody or antigen-binding fragment thereof;

D is an active drug unit;

L is any linking group, which is covalently linked to the antibody or antigen-binding fragment thereof Ab and the active drug unit D, respectively;

and, Ab is linked to one or more active drug units D through one or more linking groups L.

Further, L is covalently linked to an amino residue or a thiol residue of the antibody Ab; may be L is covalently linked to a thiol residue of the antibody Ab; may be L is covalently linked to a thiol residue formed by breaking an interchain disulfide bond of the antibody Ab.

Further, L includes a cleavable linker and a non-cleavable linker.

Further, the cleavable linker includes a peptide unit including 2 to 20 amino acids, and the peptide linker is selected from the group consisting of -valine-citrulline- (-Val-Cit-), -glycine-glycine-phenylalanine-glycine- (-Gly-Gly-Phe-Gly-), -valine-alanine- (-Val-Ala-), -valine-lysine- (-Val-Lys-), -valine-arginine- (-Val-Arg-), -phenylalanine-citrulline- (-Phe-Cit-), -phenylalanine-lysine- (-Phe-Lys-), -phenylalanine-arginine- (-Phe-Arg-) and a combination thereof.

Further, in the above-mentioned antibody-drug conjugate, L includes a structure of the following existing linkers (pages 7-10 of the specification in the Chinese Invention Patent No. CN110997010A):

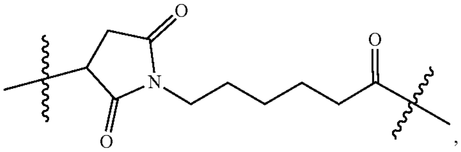
,
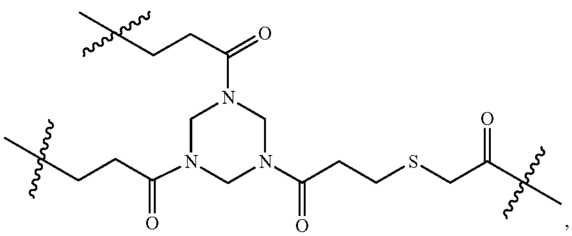
,

-continued
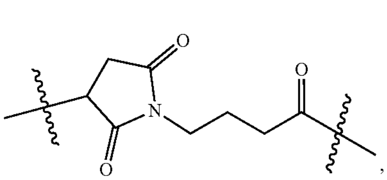,
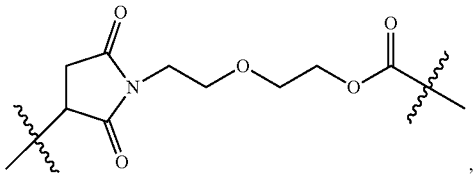,
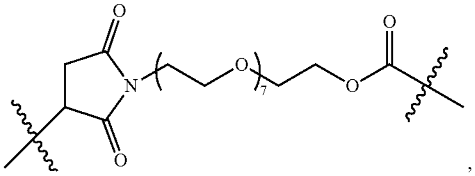,
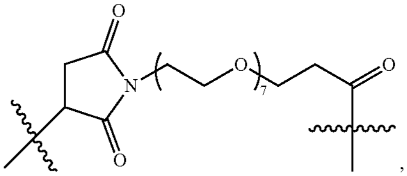,
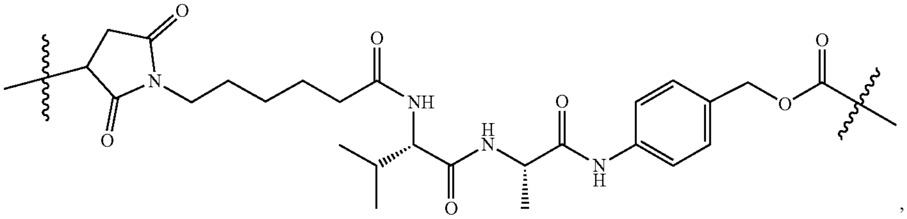,
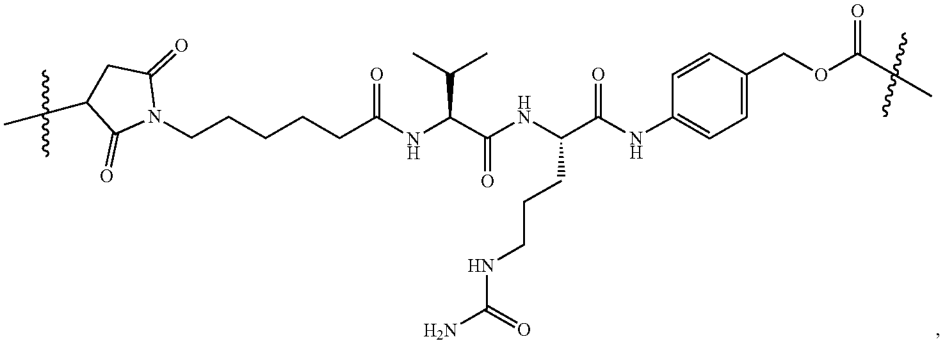,
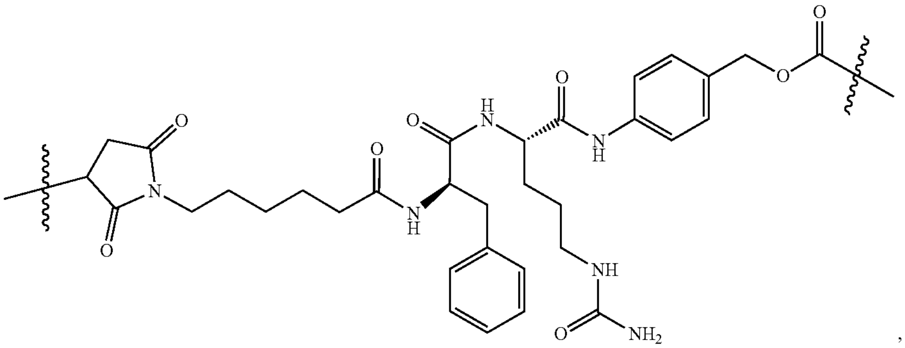,
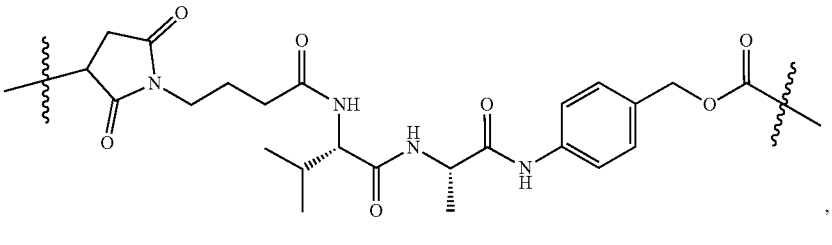, -continued
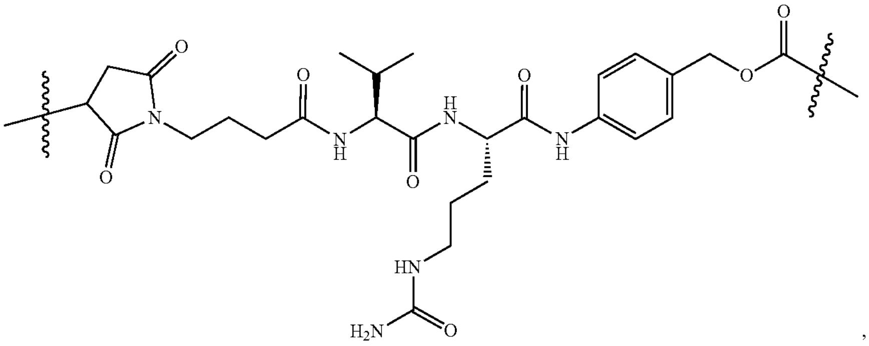
,
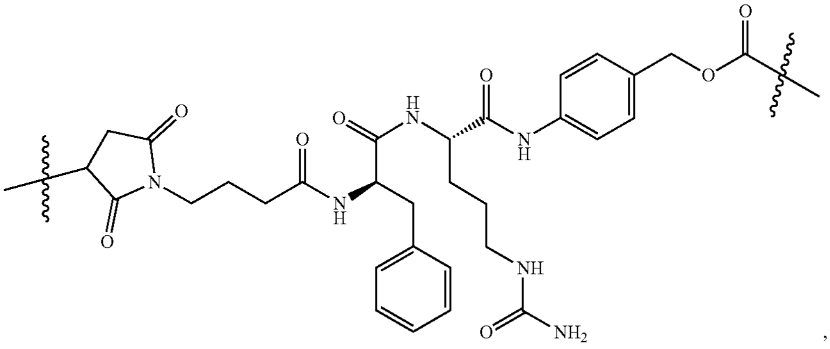
,
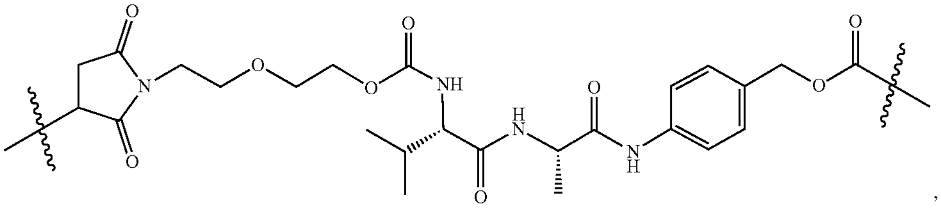
,
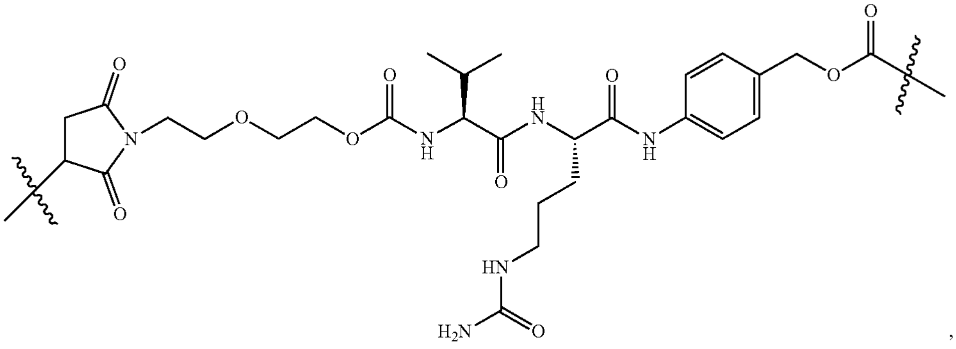
,
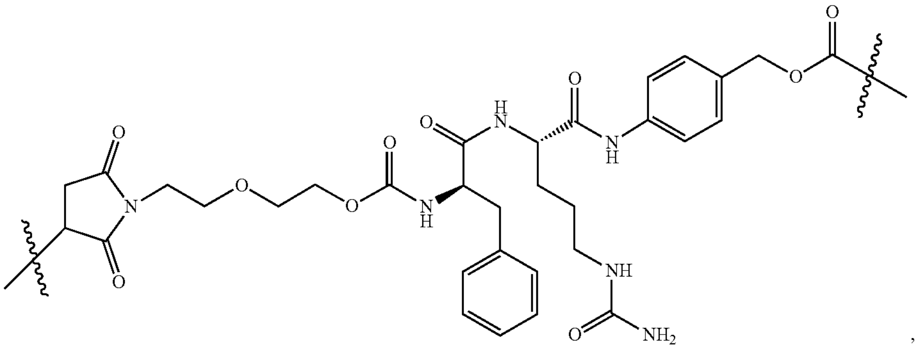
, -continued
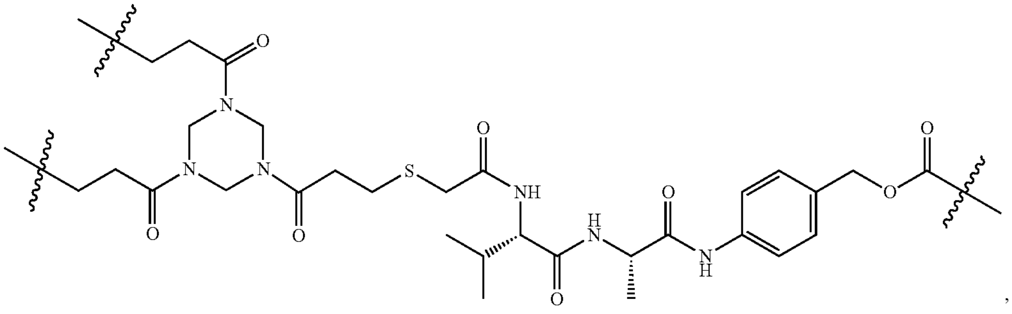
,
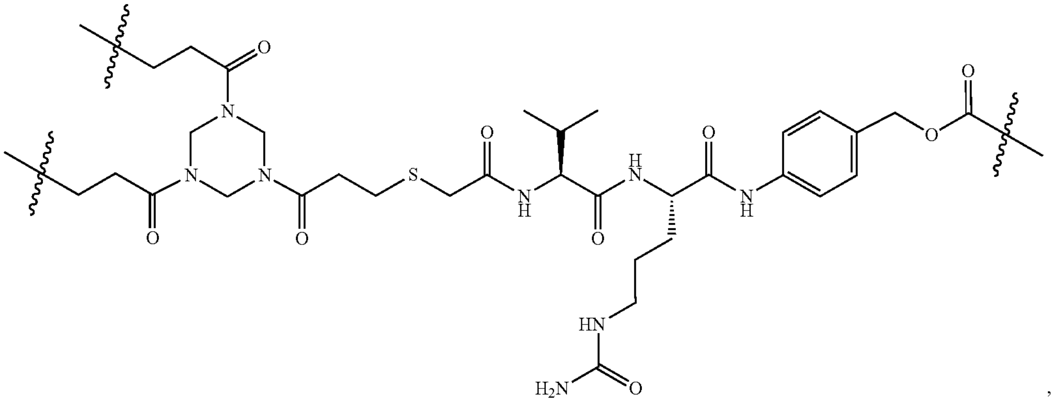
,
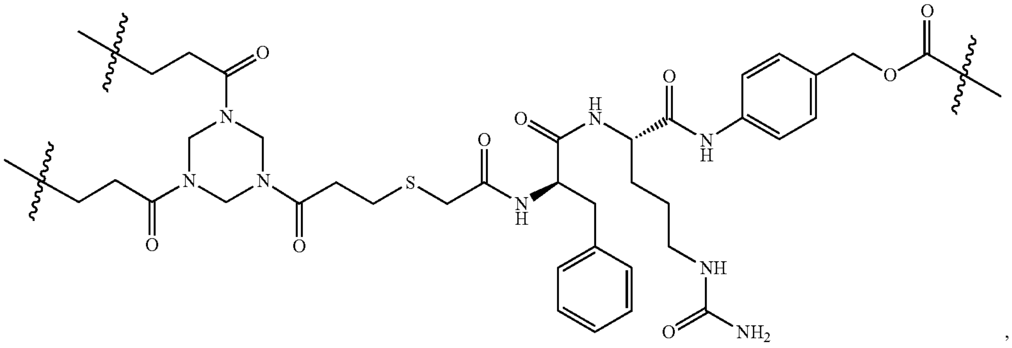
,
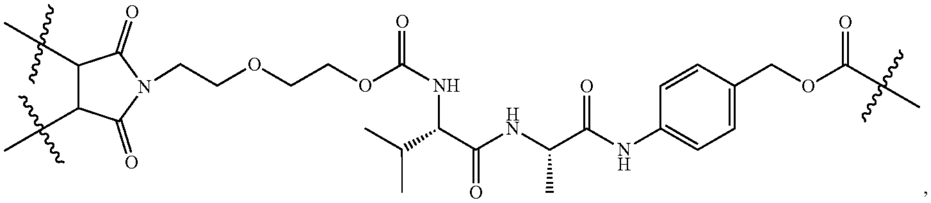
,
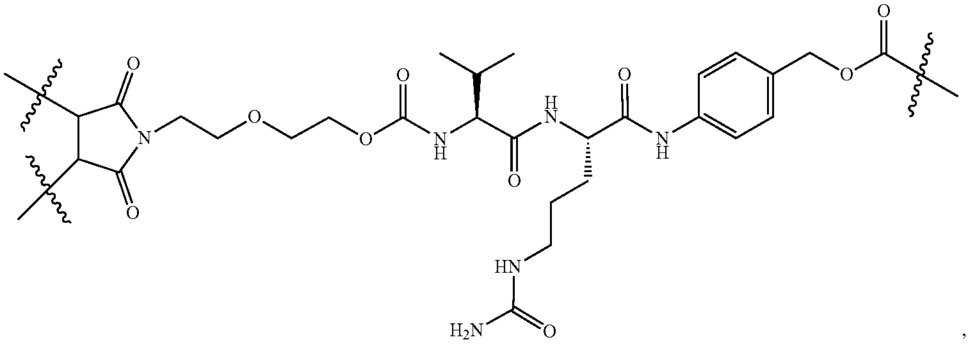
, -continued
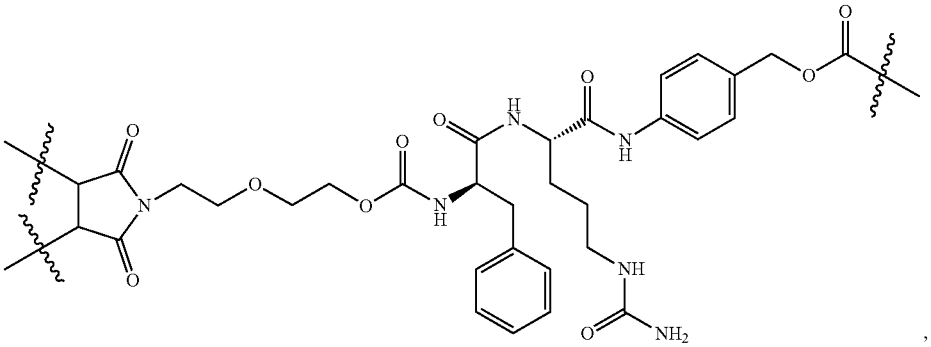
,
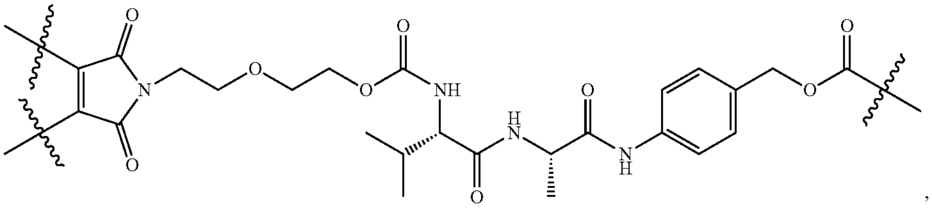
,
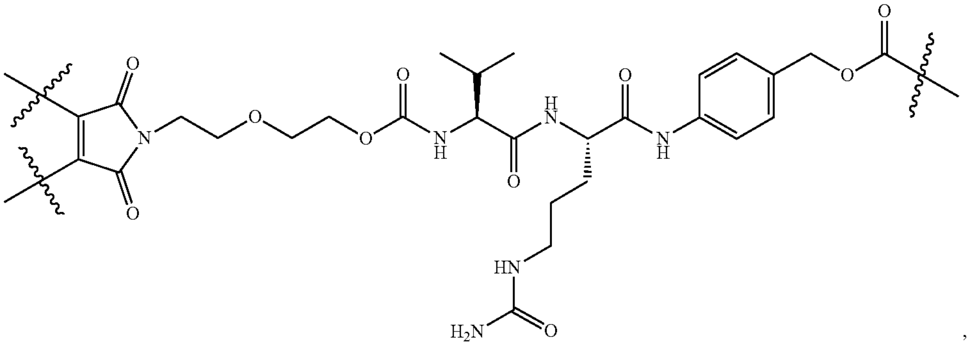
,
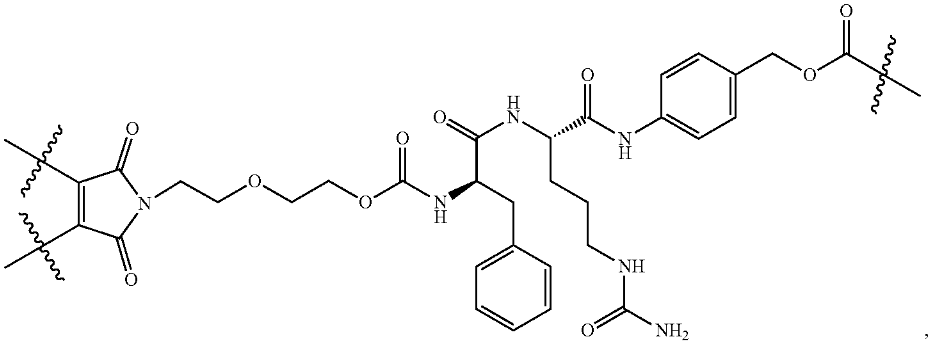
,
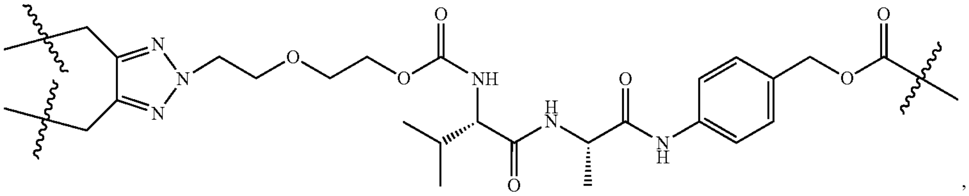
, -continued
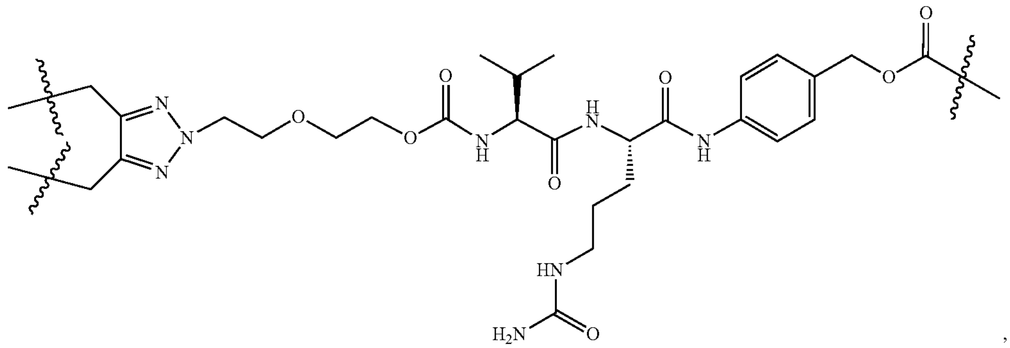
,
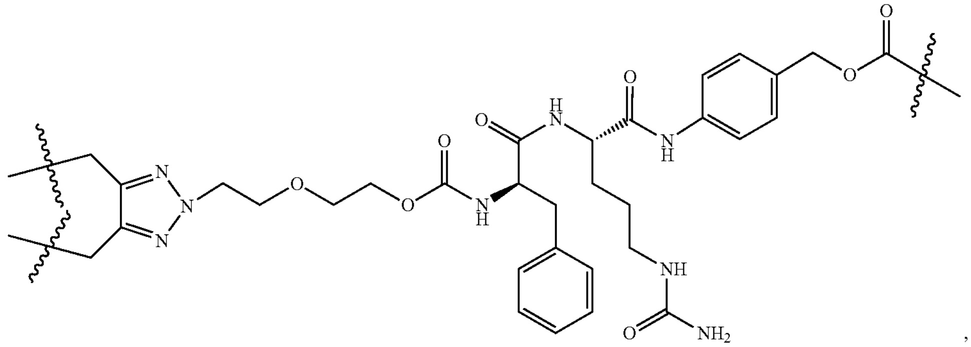
,
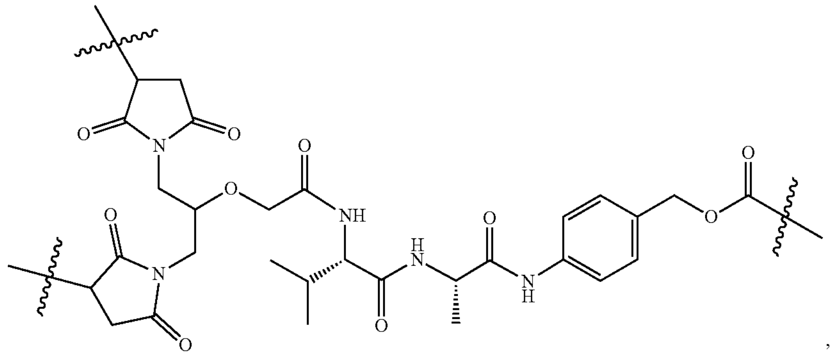
,
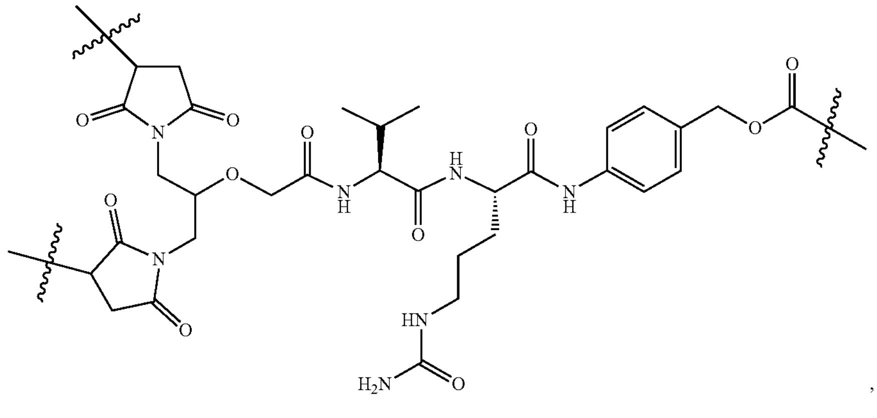
, -continued
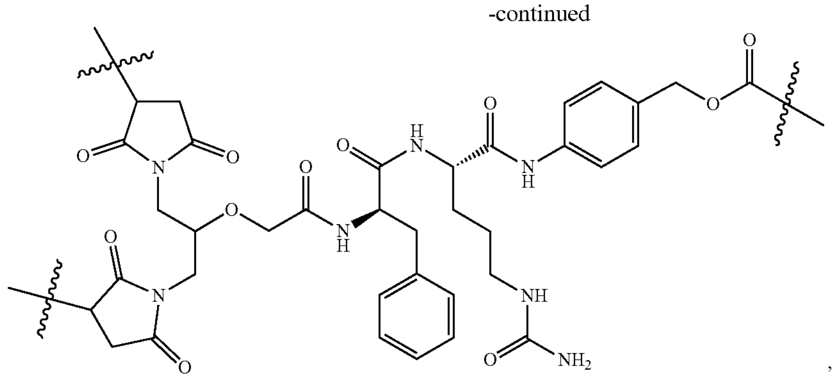
,
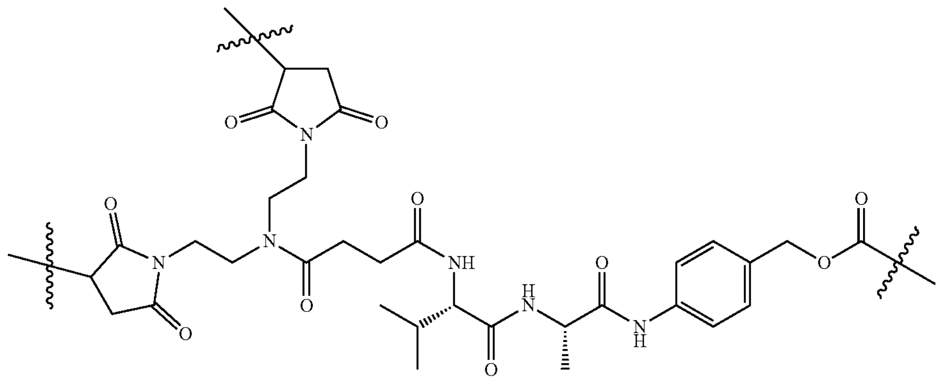
,
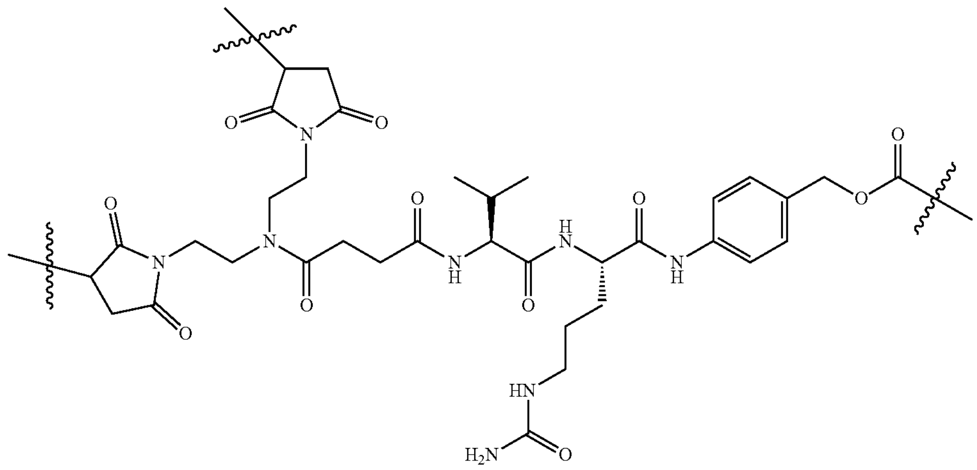
,
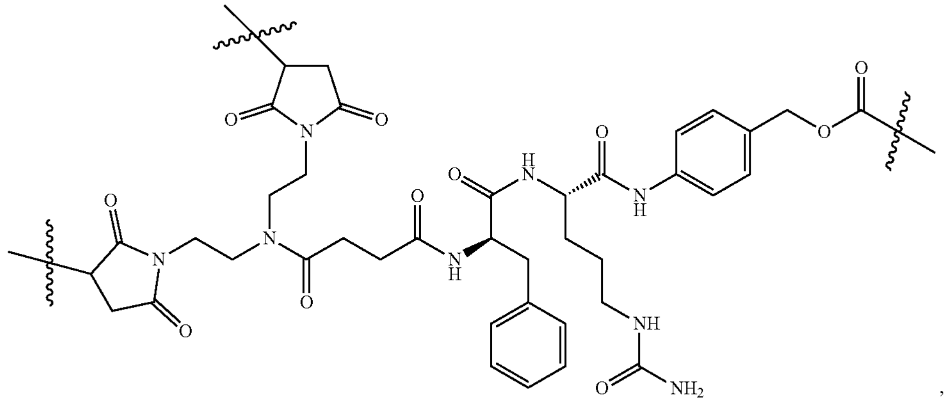
, -continued

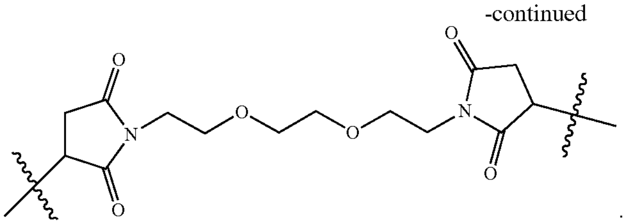

Further, the active drug unit D is selected from the group consisting of a cytotoxic molecule, cell differentiation factor, stem cell trophic factor, steroid drug, drug for the treatment of autoimmune diseases, anti-inflammatory drug, and drug for the treatment of infectious diseases; and the cytotoxic molecule includes but is not limited to a tubulin inhibitor or a DNA damaging agent; the tubulin inhibitor includes but is not limited to a cytotoxic molecule of dolastatins and auristatins, a cytotoxic molecule of maytansines; the DNA damaging agent includes but is not limited to calicheamicins, duocarmycins, anthramycin derivative pyrrolobenzodiazepine (PBD), camptothecins and a derivative thereof, and SN-38; and the cytokine molecule of auristatins includes but is not limited to MMAE, MMAF, or a derivative thereof; and the cytotoxic molecule of maytansines includes but is not limited to DM1, DM4, or a derivative thereof. Further, the active drug unit D includes the following existing active drug units used in ADC (pages 12-14 of the specification in the Chinese Invention Patent No. CN110997010A):

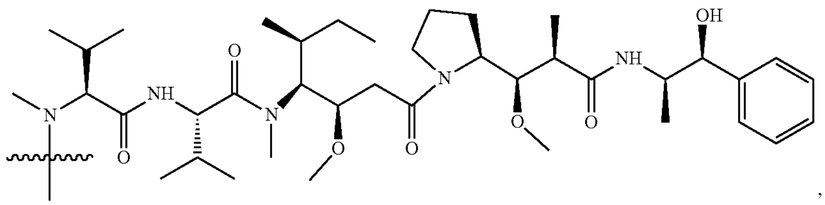

,

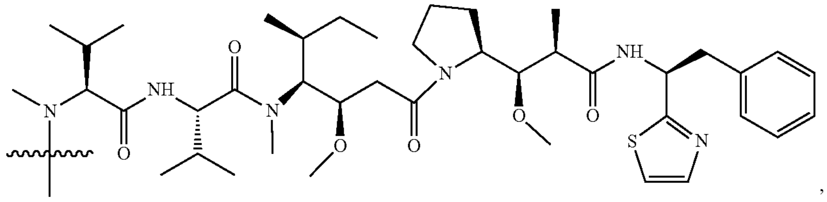

,

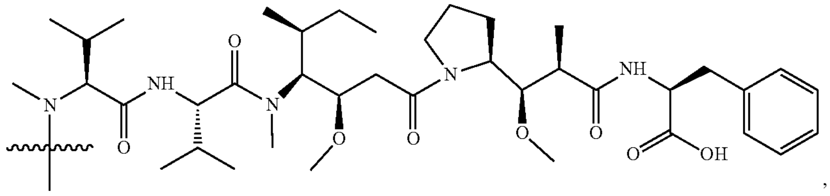

,

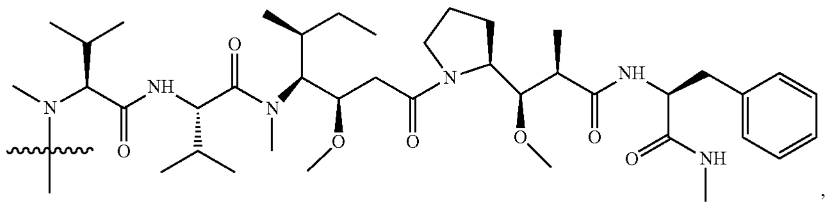

,

-continued
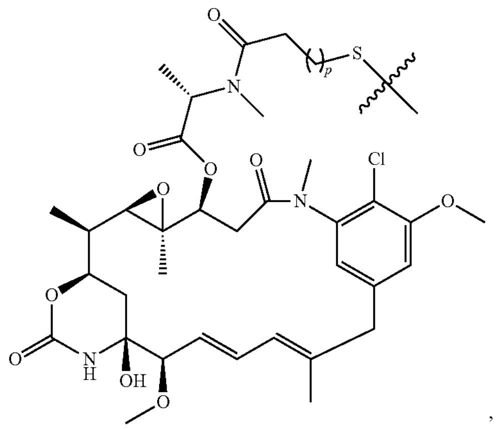
,
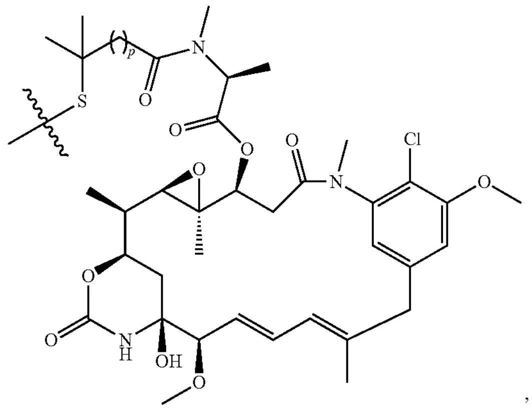
,
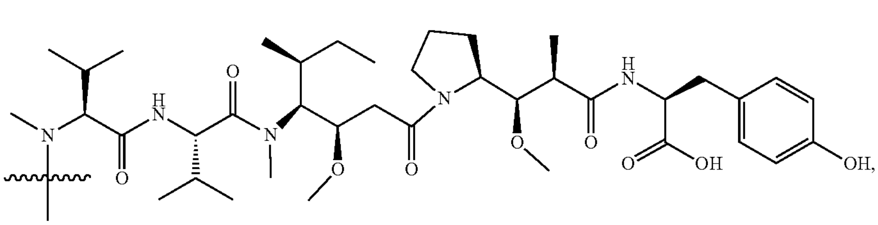
,
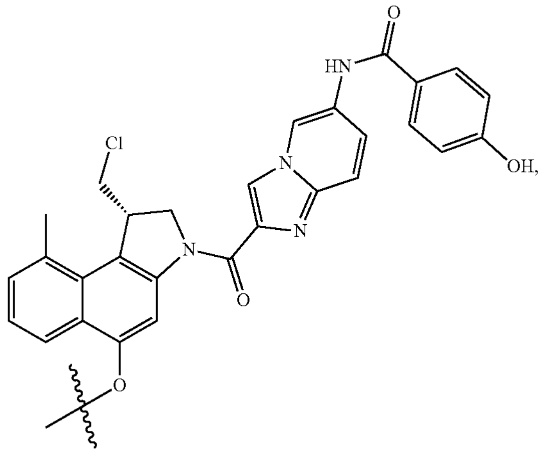
,

-continued
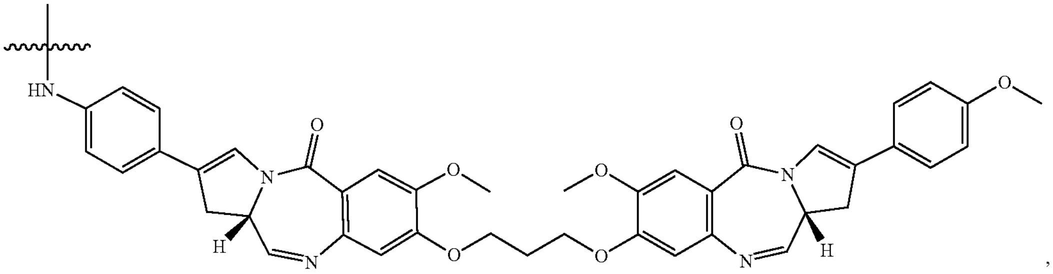
,
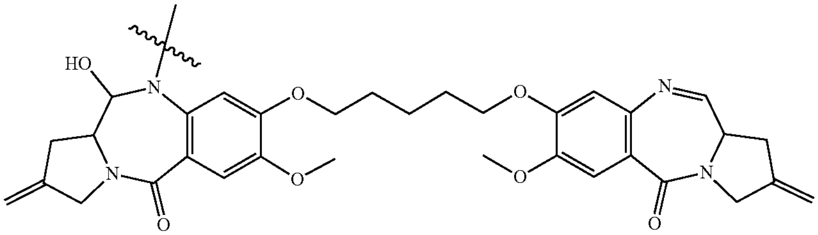
,
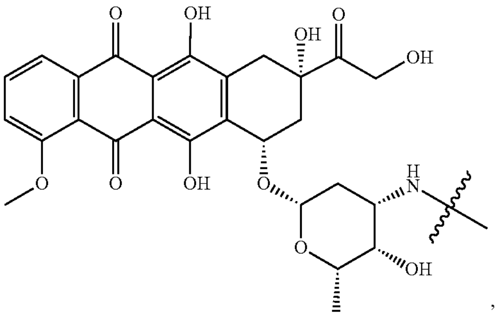
,
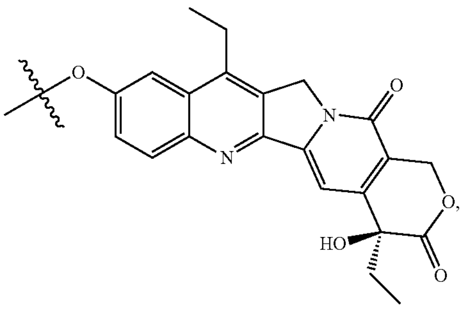
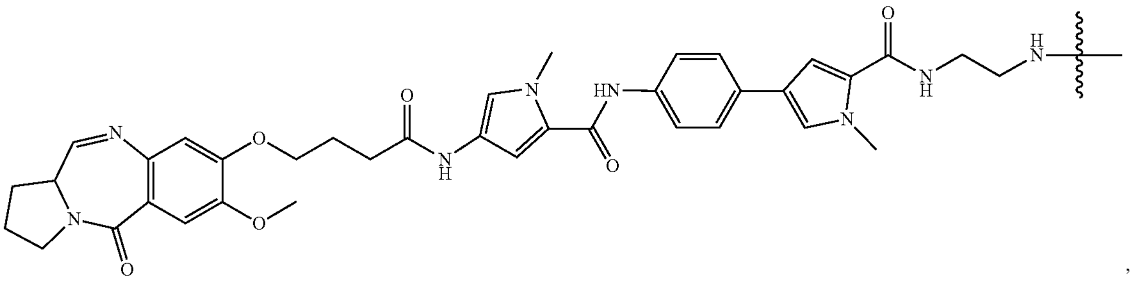
,
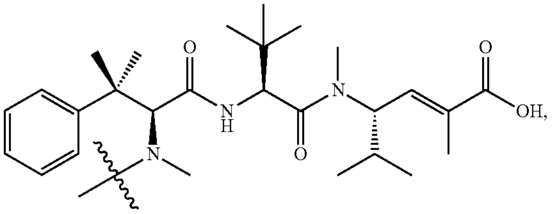

-continued
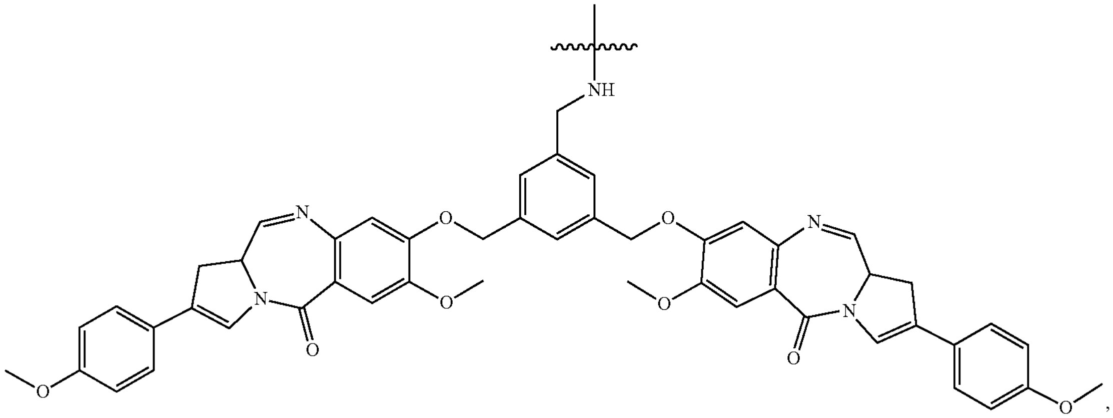
,
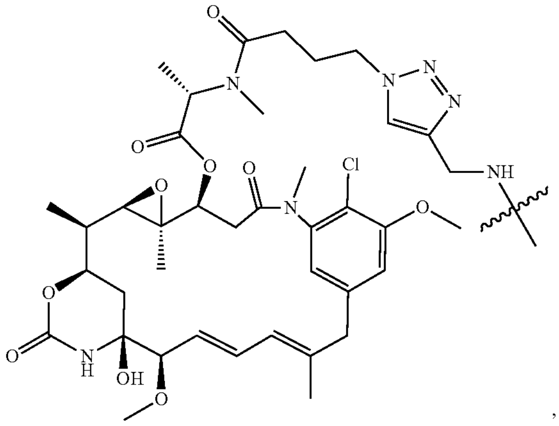
,
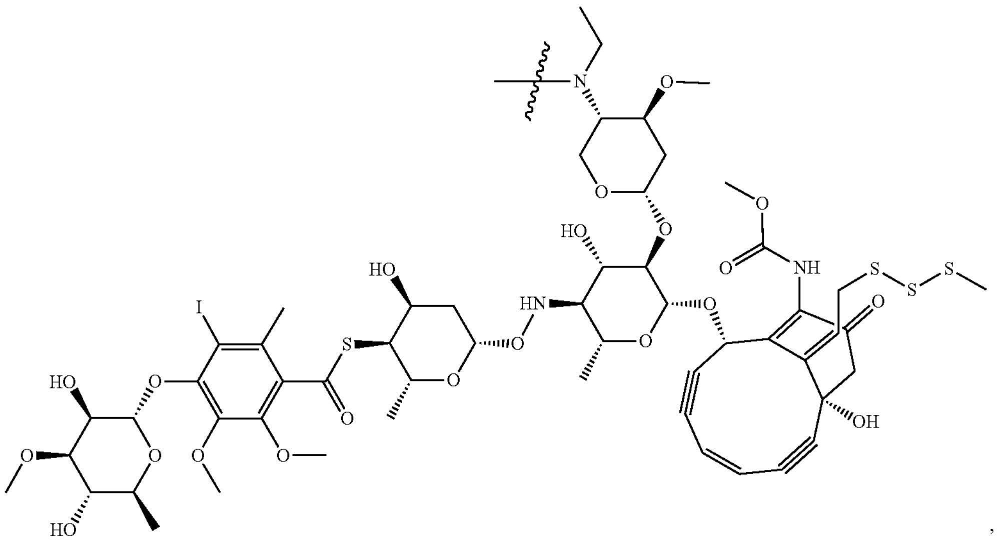
,
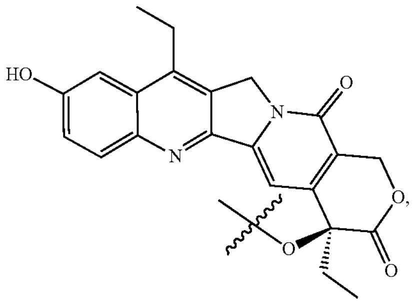

-continued
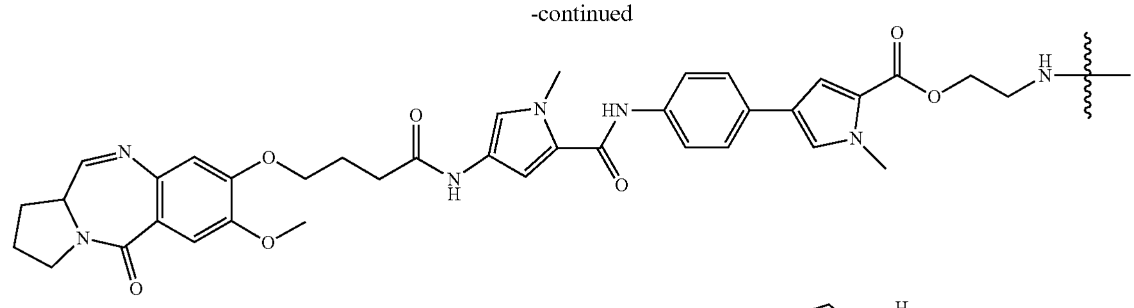
,
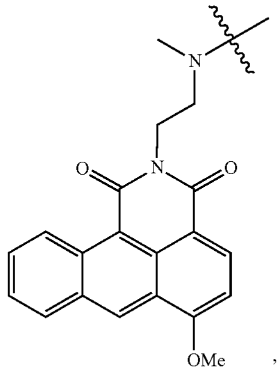
,
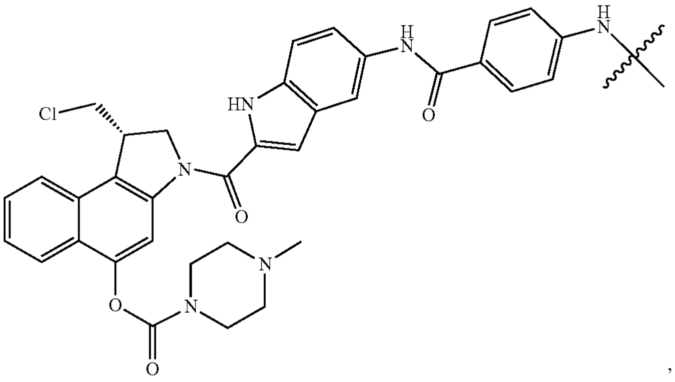
,
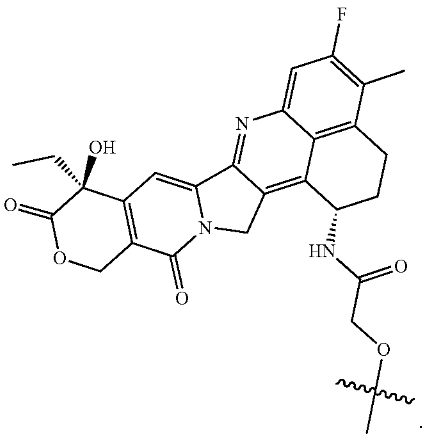
.
In some embodiments, the present disclosure provides an antibody-drug conjugate having the following structure (i.e., Ab-Mc-Val-Cit-PAB-MMAE):
ADC-1
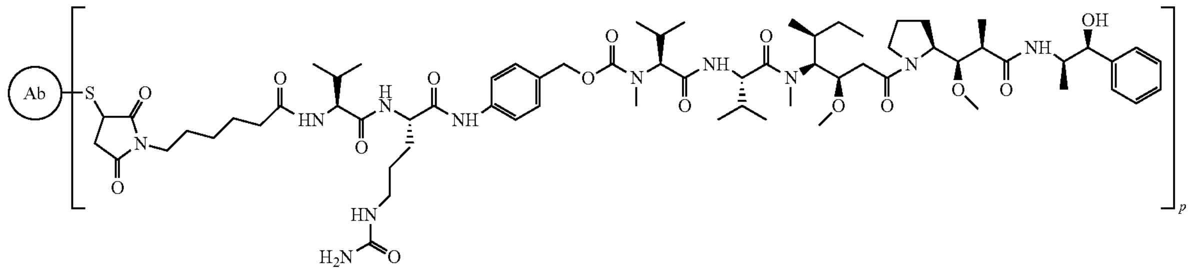
and, p is an integer selected from 1, 2, 3, 4, 5, 6, 7, and 8.

In another embodiments, the present disclosure provides an antibody-drug conjugate having the following structure (i.e., Ab-D07-Val-Cit-PAB-MMAE):

ADC-2

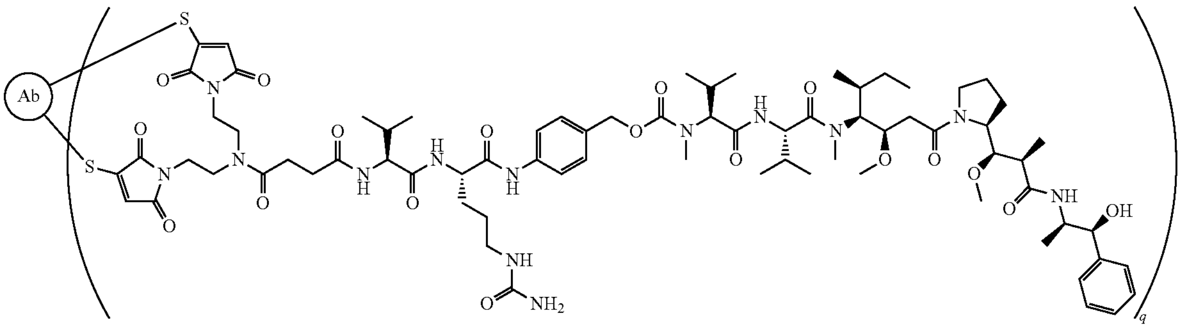

and, q is an integer selected from 1, 2, 3, and 4.

In another embodiments, the present disclosure provides an antibody drug conjugate having the following structure (i.e., Ab-PY-Val-Cit-MMAE):

ADC-3

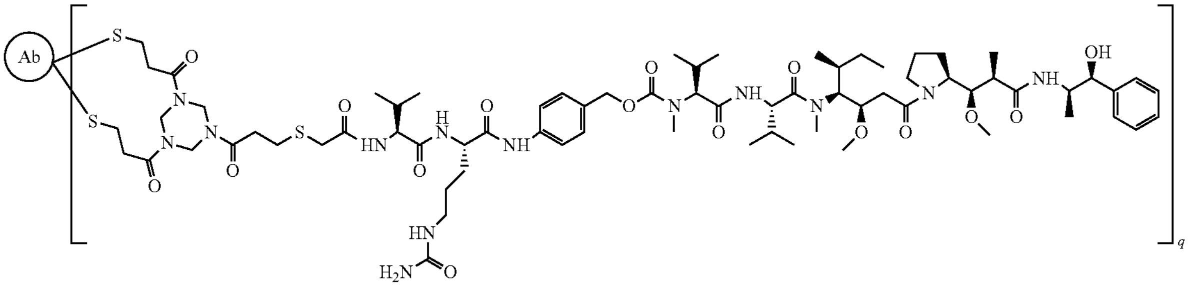

and, q is an integer selected from 1, 2, 3, and 4.

The present disclosure also provides an isolated polynucleotide encoding the above-mentioned antibody or antigen-binding fragment thereof.

The present disclosure also provides a combination of the isolated polynucleotide including a polynucleotide encoding the heavy chain of the above-mentioned antibody or antigen-binding fragment thereof, and a polynucleotide encoding the light chain of the above-mentioned antibody or antigen-binding fragment thereof.

The present disclosure also provides a nucleic acid construct including the aforementioned polynucleotide.

Further, the nucleic acid construct is a vector.

The present disclosure also provides a host cell including the aforementioned nucleic acid construct or vector.

Further, the host cell is selected from the group consisting of a prokaryotic cell, eukaryotic cell, yeast cell, mammalian cell, *E. coli* cell or CHO cell, NS0 cell, Sp2/0 cell, and BHK cell.

The present disclosure also provides a pharmaceutical composition including the above-mentioned antibody or antigen-binding fragment thereof and/or antibody-drug conjugate, and a pharmaceutically acceptable carrier.

The present disclosure also provides a method for producing an anti-Claudin 18.2 antibody, including culturing the aforementioned host cell under a condition suitable for expressing a vector encoding an anti-Claudin 18.2 antibody or an antigen-binding fragment thereof, and recovering the antibody or fragment.

The present disclosure provides use of the above-mentioned antibody or antigen-binding fragment thereof, antibody-drug conjugate, polynucleotide, polynucleotide combination, nucleic acid construct, vector, or pharmaceutical composition in the manufacture of a medicament for treating or preventing cancer, and the cancer is a solid tumor; further, the solid tumor includes gastric cancer and pancreatic cancer.

DETAILED DESCRIPTION

Definition

Figure 1:
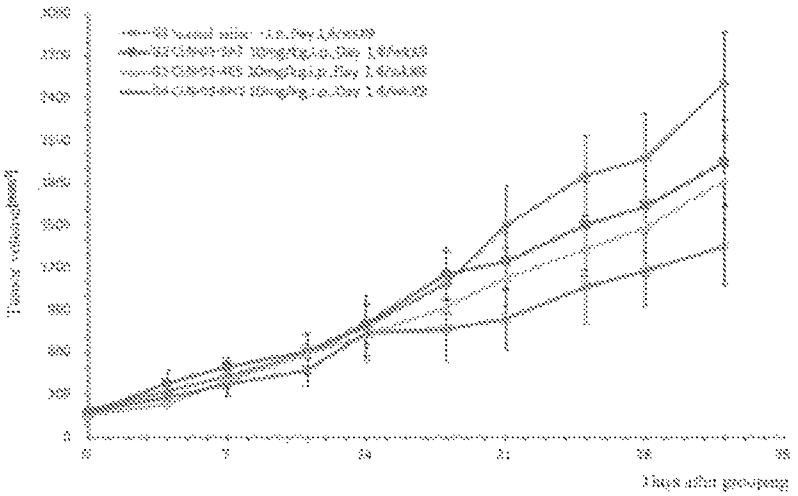
FIG. 1 is a graph showing the change in tumor volume of animals after administration of anti-Claudin 18.2 murine antibodies CLN-03-3A7, CLN-03-4E5 and CLN-03-6H2.

Unless defined otherwise, all technical and scientific terms used herein have the same meaning as understood in the art. With regard to the definitions and terms in the art, reference may be made to Current Protocols in Molecular Biology (Ausubel). The standard three- and/or one-letter code used for expressing one of 20 common L-amino acids in the art is adopted as the abbreviation of an amino acid residue.

In the present disclosure, a method for determining or numbering the complementarity determining region (CDR) of an antibody's variable domain includes IMGT, Kabat, Chothia, AbM and Contact, which are well known in the art.

For the purposes of the present disclosure, the "consistency", "identity" or "similarity" between two nucleic acid or amino acid sequences refers to the percentage of identical nucleotides or identical amino acid residues between the two sequences to be compared after optimal alignment. The percentage is purely statistical and the differences between the two sequences are randomly distributed and cover their full length. Sequence comparison between two nucleic acid or amino acid sequences are usually performed by comparing these sequences after they have been optimally matched, and the comparison can be performed on a segment or on a "comparison window". In addition to manual implementation, the optimal alignment for comparing sequences can also be performed by the local homology algorithm of Smith and Waterman (1981) [Ad. App. Math. 2: 482], the local homology algorithm of Neddleman and Wunsch (1970) [J. Mol. Biol. 48: 443], the similarity search method of Pearson and Lipman (1988) [Proc. Natl. Acad. Sci. USA 85: 2444), or a computer software using these algorithms (GAP, BESTFIT, FASTA and TFASTA in the Wisconsin Genetics Software Package, Genetics Computer Group, 575 Science Dr., Madison, WI, or BLAST N or BLAST P comparison software).

As used herein, "antibody" is used in a broadest sense and encompasses various antibodies including, but not limited to, a monoclonal antibody and a multispecific antibody (e.g., a bispecific antibody). As used herein, "antigen-binding fragment" refers to an antibody fragment consisting of or including a partial sequence of a heavy or light variable chain of an antibody from which it is derived, and the partial sequence for retaining the same binding specificity as the antibody from which it is derived and a sufficient affinity, may be equal to at least 1/100, may be at least 1/10 of the affinity of the antibody from which it is derived. Such a functional fragment includes a minimum of 5 amino acids, and 10, 15, 25, 50 or 100 contiguous amino acids of the antibody sequence from which it is derived, including (particularly) Fab, F(ab'), $F(ab')_2$, Fv, dAb, Fd, a complementarity determining region (CDR) fragment, a single chain antibody (scFv), and a bivalent single chain antibody, that contains at least an immunoglobulin fragment enough to allow a specific antigen to bind to the polypeptide. The above fragments can be prepared by a synthetic or enzymatic method, or by chemical cleavage of an intact immunoglobulin, or can be genetically engineered by recombinant DNA technology. The preparation methods thereof are well known in the art. A heavy chain contains a heavy chain variable region (abbreviated as VH) and a heavy chain constant region. The heavy chain constant region contains three domains, CH1, CH2 and CH3. A light chain contains a light chain variable region (abbreviated as VL) and a light chain constant region. The light chain constant region contains a domain, CL. VH and VL regions can be further subdivided into multiple regions with high variability, called as complementarity determining regions (CDRs), interspersed with more conservative regions called as framework regions (FRs). Each VH and VL is composed of three CDRs and four FRs, which are arranged from the amino terminal to the carboxy terminal in the following order: FR1, CDR1, FR2, CDR2, FR3, CDR3, FR4. These variable regions of the heavy and light chains contain a binding domain that interacts with an antigen. The constant region of an antibody can mediate binding of an immunoglobulin to a host tissue or factor, including various cells in the immune system (such as effector cells) and the first component of the classical complement system (Clq). Chimeric or humanized antibodies are also encompassed by the antibodies according to the present disclosure.

The term "humanized antibody" refers to an antibody that contains a CDR region derived from a non-human antibody, with the rest deriving from one (or several) human antibody. In one embodiment, in order to retain binding affinity, some residues at the backbone (called FR) segment can be modified (Document 8: Jones et al., Nature, 321: 522-525, 1986; Verhoeyen et al., Science, 239: 1534-1536, 1988; Riechmann et al., Nature, 332: 323-327, 1988.). Humanized antibodies or fragments thereof according to the present disclosure can be prepared by techniques known in the art (Document 9: Singer et al., J. Immun. 150: 2844-2857, 1992; Mountain et al., Biotechnol. Genet. Eng. Rev., 10: 1-142, 1992; or Bebbington et al., Bio/Technology, 10: 169-175, 1992.).

The term "chimeric antibody" refers to an antibody in which the variable region sequence is from one species while the constant region sequence is from another species, for example, an antibody in which the variable region sequence is from a mouse antibody while the constant region sequence is from a human antibody. A chimeric antibody or a fragment thereof according to the present disclosure can be prepared by using genetic recombination technology. For example, the chimeric antibody can be produced by cloning a recombinant DNA including a promoter and a sequence encoding a variable region of a non-human, especially a murine monoclonal antibody according to the present disclosure, and a sequence encoding a constant region of a human antibody. The chimeric antibody of the present disclosure encoded by such a recombinant gene will be, for example, a murine-human chimera whose specificity is determined by the variable region derived from murine DNA, and the isotype is determined by the constant region derived from human DNA. For methods for preparing a chimeric antibody, for example, reference can be made to the document Verhoeyn et al. (BioEssays, 8:74, 1988).

The term "monoclonal antibody" refers to a preparation of an antibody molecule consisting of a single molecule.

Monoclonal antibody compositions display a single binding specificity and affinity for a particular epitope.

The term an "isolated" nucleic acid molecule refers to a nucleic acid molecule identified and separated from at least one contaminant nucleic acid molecules, and is generally associated with the contaminant nucleic acid molecule in the natural source of an antibody nucleic acid. An isolated nucleic acid molecule is different in form or environment from when it is found in nature, and therefore different from that existing in natural cells. However, an isolated nucleic acid molecule includes a nucleic acid molecule contained in cells where an antibody is usually expressed, and where for example, it is located on a different chromosomal position from that in a natural cell.

Generally, in order to prepare a monoclonal antibody or functional fragment thereof, especially a murine-derived monoclonal antibody or functional fragment thereof, reference can be made to the technology especially described in the manual "Antibodies" (Document 10: Harlow and Lane, Antibodies: A Laboratory Manual, Cold Spring Harbor Laboratory, Cold Spring Harbor NY, pp. 726, 1988) or the technique for preparation from hybridoma cells described by Kohler and Milstein (Nature, 256: 495-497, 1975).

EXAMPLE

The embodiments of the present disclosure will be described in detail below in conjunction with examples. However, it will be understood in the art that the following examples are only used to illustrate the present disclosure and should not be regarded as limiting the scope of the present disclosure.

Example 1 Screening and Affinity Detection of Anti-Claudin 18.2 Murine Antibody Claudin 18.2-knockout mice (from Biocytogen (Beijing) Pharmaceutical Technology Co., Ltd.) were immunized with cells including a eukaryotic expression plasmid encoding the first extracellular domain of Claudin 18.2 as an immunogen.

A total of 22 murine antibodies were screened: CLN-40-3C8, CLN-07-4C3, CLN-39-8D11, CLN-39-1E1, CLN-03-6H2, CLN-03-4E5, CLN-03-1A8, CLN-03-4A11, CLN-07-5B10, CLN-07-5G11, CLN-03-3A7, CLN-03-4C11, CLN-38-4H3, CLN-03-4G7, CLN-39-1B6, CLN-39-3E7, CLN-03-1F5, CLN-38-8A1, CLN-39-7H7, CLN-03-6G10, CLN-40-6C9 and CLN-07-5D9.

The binding activity of the obtained 22 murine antibodies to Claudin 18.2 was detected by FACS. The samples were diluted to the final concentration of 10 μg/mL, 1 μg/mL, 0.1 μg/mL, 0.01 μg/mL, and 0.001 μg/mL, and reacted with CHO-Claudin 18.2 cells at 4° C. for 30 min, respectively. After centrifugation and removal of the supernatant, each well was added with 200 μL of PBS, centrifuged at 2000 rpm for 5 min, and washed twice. Then, each well was added with 50 μL of 1:100 diluted anti-mouse IgGFc-FITC antibody (Abeam, Cat. No. ab97264) at 4° C. for 30 min of reaction, then washed once by repeating the washing step, and finally added with 200 μL of PBS to resuspend for the detection by the machine. The detection results are shown in Table 3, indicating that multiple antibodies showed good binding activity.

TABLE 3

Detection results of affinity of anti-Claudin 18.2 murine antibody

| | Cell binding activity $EC_{50}$ | |
|---|---|---|
| Clone No. | μg/mL | nM |
| CLN-40-3C8 | 0.5022 | 0.335 |
| CLN-07-4C3 | 0.703 | 0.469 |
| CLN-39-8D11 | 0.8661 | 0.557 |
| CLN-39-1E1 | 0.8726 | 0.582 |
| CLN-03-6H2 | 1.168 | 0.779 |
| CLN-03-4E5 | 1.281 | 0.854 |
| CLN-03-1A8 | 1.367 | 0.911 |
| CLN-03-4A11 | 1.373 | 0.915 |
| CLN-07-5B10 | 1.511 | 1.007 |
| CLN-07-5G11 | 1.601 | 1.067 |
| CLN-03-3A7 | 2.386 | 1.59 |
| CLN-03-4C11 | 2.655 | 1.77 |
| CLN-38-4H3 | 2.792 | 1.86 |
| CLN-03-4G7 | 3.337 | 2.22 |
| CLN-39-1B6 | 3.635 | 2.43 |
| CLN-39-3E7 | 3.676 | 2.42 |
| CLN-03-1F5 | 4.259 | 2.83 |
| CLN-38-8A1 | 4.806 | 3.2 |
| CLN-39-7H7 | 5.154 | 3.43 |
| CLN-03-6G10 | 6.054 | 4.03 |
| CLN-40-6C9 | 7.185 | 4.78 |
| CLN-07-5D9 | 9.093 | 6.06 |

Example 2 In Vivo Efficacy Evaluation of Anti-Claudin 18.2 Murine Antibody 11 anti-Claudin 18.2 murine antibodies with good affinity (CLN-40-3C8, CLN-07-4C3, CLN-39-8D11, CLN-39-1E1, CLN-03-6H2, CLN-03-4E5, CLN-03-1A8, CLN-03-4A11, CLN-07-5B10, CLN-07-5G11 and CLN-03-3A7) were selected. Through gastric cancer PDX model, CLN-03-3A7, CLN-03-4E5 and CLN-03-6H2 were determined with therapeutic potential, and thus the above three antibodies were subjected to the subsequent in vivo efficacy evaluation.

Figure 2:
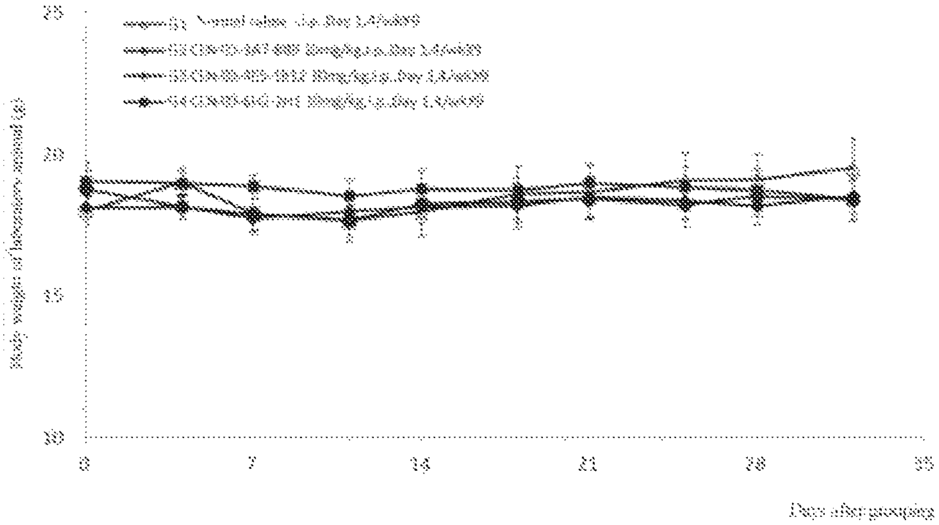
FIG. 2 is a graph showing the change in body weight of animals after administration of anti-Claudin 18.2 murine antibodies CLN-03-3A7, CLN-03-4E5 and CLN-03-6H2.

B-NDG mice (this mouse model was provided by Biocytogen Jiangsu Gene Biotechnology Co., Ltd.) were subcutaneously inoculated with gastric cancer tumor, and divided into groups when the tumor volume reached 150 $mm^3$, with 5 mice in each experimental group. After grouping, the murine antibodies CLN-03-3A7, CLN-03-4E5 and CLN-03-6H2 with good endocytosis and binding performance were injected into the abdominal cavity of mice at a dose of 10 mg/kg twice a week. The tumor growth of the mice was monitored twice a week (tumor volume=0.5*long diameter*short diameter2). The specific results are shown in FIG. 1 and FIG. 2. The experimental results show that the Claudin 18.2 murine antibody had a significant inhibitory effect on tumors and had a good safety, with the body weight of the mice not changing significantly, and the anti-tumor activity of the three murine antibodies was as follows: CLN-03-6H2>CLN-03-4E5>CLN-03-3A7.

Example 3 Preparation and Affinity Detection of Chimeric Antibody

Figure 3:
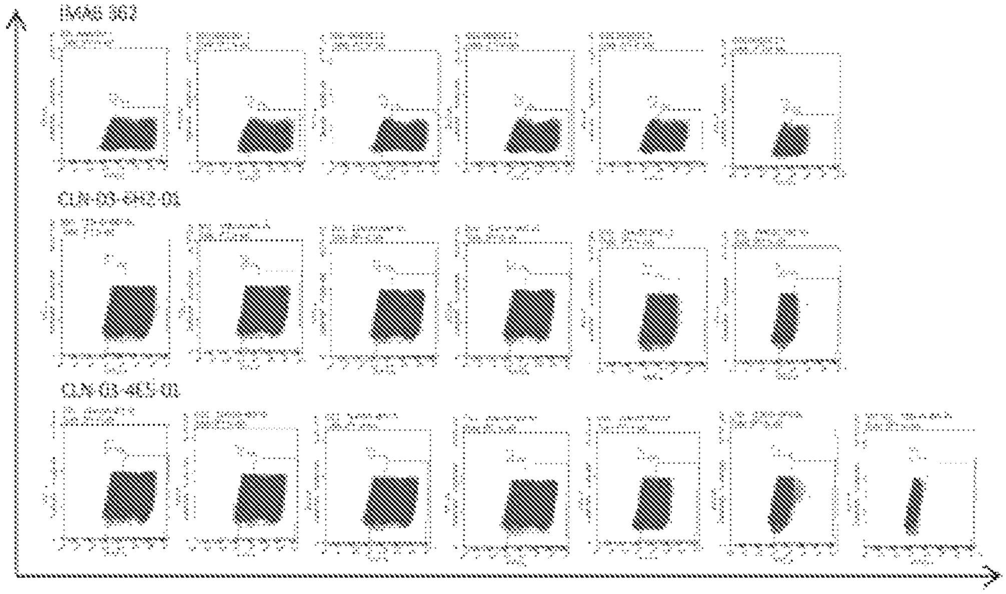
FIG. 3 is a graph showing the comparison of the detected affinity of chimeric antibodies CLN-03-4E5-01, CLN-03-6H2-01 and IMAB362.

Two murine antibodies CLN-03-4E5 and CLN-03-6H2 were subjected to chimeric antibody modification to obtain chimeric antibodies CLN-03-4E5-01 and CLN-03-6H2-01, respectively. The affinities of CLN-03-4E5-01, CLN-03-6H2-01 and IMAB362 (human-murine chimeric monoclonal antibody, claudiximab) were compared. It can be seen from the results (as shown in Table 4 and FIG. 3) that CLN-03-4E5-01, CLN-03-6H2-01 and IMAB362 all showed good affinity activities, and both of the two chimeric antibodies CLN-03-4E5-01 and CLN-03-6H2-01 provided by the present disclosure had a better binding activity than IMAB362.

TABLE 4

Affinity $EC_{50}$ value of chimeric antibody and IMAB362

| Name | $EC_{50}$ value (μg/mL) |
|---|---|
| CLN-03-4E5-01 | 0.4475 |
| CLN-03-6H2-01 | 0.4103 |
| IMAB362 | 0.475 |

Example 4 Endocytosis Efficiency Detection of Chimeric Antibody

Figure 4A:
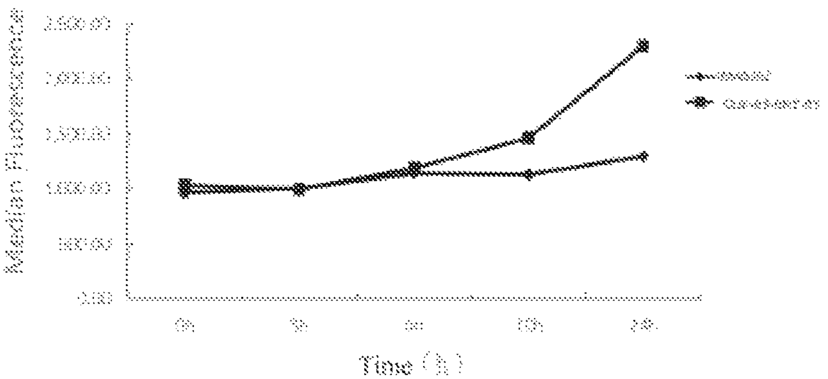
FIG. 4A is a graph showing the comparison of the endocytosis efficiency of CLN-03-6H2-01 and IMAB362 in the gastric cancer model KATOIII.
Figure 4B:
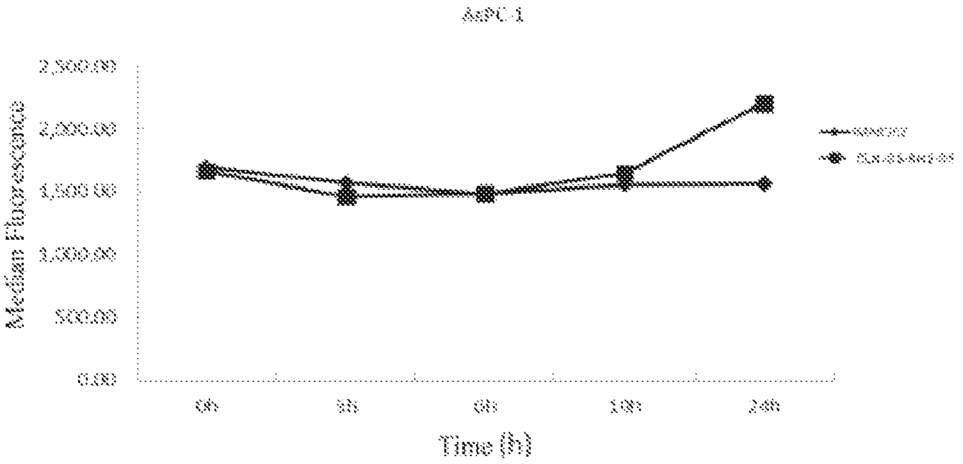
FIG. 4B is a graph showing the comparison of the endocytosis efficiency of CLN-03-6H2-01 and IMAB362 in the pancreatic cancer model AsPC-1.
Figure 4C:
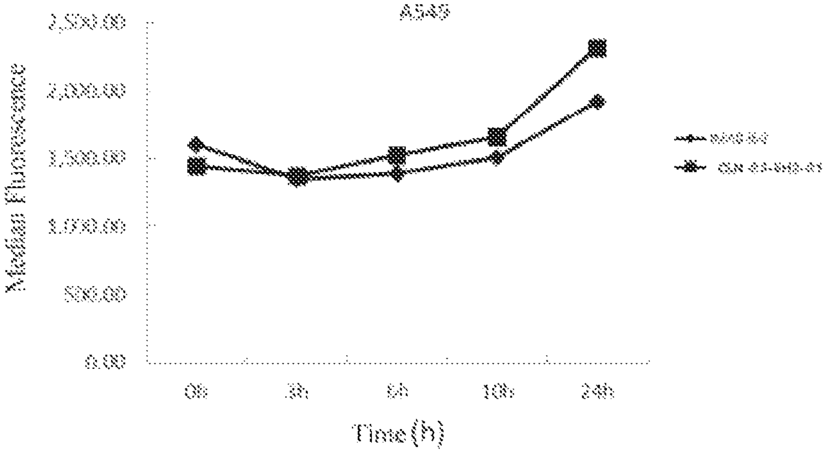
FIG. 4C is a graph showing the comparison of the endocytosis efficiency of CLN-03-6H2-01 and IMAB362 in the lung cancer model A549.

The endocytosis efficiency of the chimeric antibody CLN-03-6H2-01 and IMAB362 (human-murine chimeric monoclonal antibody, claudiximab) was detected and compared. The purified chimeric antibody was labeled according to the instructions of promega PHAb antibody dye labeling kit (Promega G9841), and the concentration of the antibody before the labeling was 2 mg/mL. The labeled antibody was incubated with cells of gastric cancer model KATOIII (ATCC), pancreatic cancer model AsPC-1 (ATCC), and lung cancer model A549 (ATCC) according to a certain concentration gradient at 37° C. The time gradient was set as: 0 h, 2 h, 4 h, 6 h, 8 h, 12 h, and 24 h, and the concentration gradient was set as: 0.1 nM, 1 nM, and 10 nM. After sampling at each point, the fluorescence intensity was detected by a flow cytometer. The experimental results (see FIG. 4A, FIG. 4B and FIG. 4C) show that the chimeric antibody CLN-03-6H2-01 had a better endocytosis effect than IMAB362 in different tumor cell lines, where FIG. 4A shows the comparison of the endocytosis efficiency of CLN-03-6H2-01 and IMAB362 in the gastric cancer model KATOIII, FIG. 4B shows the comparison of the endocytosis efficiency of CLN-03-6H2-01 and IMAB362 in the pancreatic cancer model AsPC-1, and FIG. 4C shows the comparison of the endocytosis efficiency of CLN-03-6H2-01 and IMAB362 in the lung cancer model A549.

Example 5 Humanization of Chimeric Antibody CLN-03-6H2-01

The chimeric antibody CLN-03-6H2-01 was humanized by grafting CDRs of light or heavy chain into the framework region of light or heavy chain of immunoglobulin. The CDRs of the light chain and heavy chain of the chimeric antibody CLN-03-6H2-01 were determined using the Kabat system. The human IgG1 framework region was determined by alignment in a database of antibody variable regions. The light chain variable region sequences of different humanized Clandin 18.2 antibodies and the heavy chain variable region sequences of different humanized Clandin 18.2 antibodies were designed and synthesized. The light chain variable region of the humanized Clandin 18.2 antibody was fused with the human kappa constant region by PCR to obtain the light chain of the humanized Clandin 18.2 antibody in full length. The heavy chain variable region of the humanized Clandin 18.2 was fused with the IgG1 constant region by PCR to obtain the heavy chain of the humanized Clandin 18.2 antibody in full length. Different light and heavy chains were combined and expressed, and the affinities of multiple purified humanized antibodies were detected by flow cytometry (FACS) (see Table 5). The antibody H-1 having the best affinity (named as RGCLN18.2 antibody) was selected for sequencing.

TABLE 5

Comparison of affinity of humanized chimeric antibody CLN-03-6H2-01

| Humanized antibody No. | $EC_{50}$ (μg/mL) |
|---|---|
| H-1 | 0.1656 |
| H-2 | 0.2443 |
| H-3 | 0.3006 |
| H-4 | 0.3120 |
| H-5 | 0.3969 |
| H-6 | 0.3971 |
| H-7 | 0.4884 |
| H-8 | 0.5953 |
| H-9 | 0.8415 |
| H-10 | 0.8469 |
| H-ll | 1.009 |
| H-12 | 1.122 |
| H-13 | 1.541 |
| H-14 | 1.636 |
| H-15 | 1.940 |
| CLN-03-6H2-01 | 0.462 |

Table 6 shows the amino acid sequences of CDRs of light and heavy chains of RGCLN18.2 antibody (Kabat numbering).

TABLE 6

Amino acid sequences of CDRs of heavy and light chains of RGCLN18.2 antibody (Kabat numbering)

| | | |
|---|---|---|
| Heavy chain | CDR1 SEQ ID NO: 5 | NYLIE |
| | CDR2 SEQ ID NO: 10 | LINPGSGGTNYNEKFKG |
| | CDR3 SEQ ID NO: 15 | GGYYGNSFAY |
| Light chain | CDR1 SEQ ID NO: 20 | KSSQSLLNSGNQKNYLT |
| | CDR2 SEQ ID NO: 25 | WASTRES |
| | CDR3 SEQ ID NO: 30 | QNAYYYPYT |

Amino acid sequence of the heavy chain variable region of RGCLN18.2 antibody (SEQ ID NO: 1):

```
QVQLVQSGAE VKKPGASVKV SCKASGYAFT NYLIEWVRQA PGQGLEWMGL INPGSGGTNY  60
NEKFKGRVTM TRDTSTSTVY MELSSLRSED TAVYYCARGG YYGNSFAYWG QGTLVTVSS  119
```

Amino acid sequence of the light chain variable region of RGCLN18.2 antibody (SEQ ID NO: 2):

```
DIVMTQSPLS LPVTPGEPAS ISCKSSQSLL NSGNQKNYLT WYLQKPGQSP QLLIYWASTR  60
ESGVPDRFSG SGSGTDFTLK ISRVEAEDVG VYYCQNAYYY PYTFGGGTKV EIK        113
```

Amino acid sequence of the heavy chain of RGCLN18.2 antibody (SEQ ID NO: 33):

```
QVQLVQSGAE VKKPGASVKV SCKASGYAFT NYLIEWVRQA PGQGLEWMGL INPGSGGTNY  60
NEKFKGRVTM TRDTSTSTVY MELSSLRSED TAVYYCARGG YYGNSFAYWG QGTLVTVSSA 120
STKGPSVFPL APSSKSTSGG TAALGCLVKD YFPEPVTVSW NSGALTSGVH TFPAVLQSSG 180
LYSLSSVVTV PSSSLGTQTY ICNVNHKPSN TKVDKKVEPK SCDKTHTCPP CPAPELLGGP 240
SVFLFPPKPK DTLMISRTPE VTCVVVDVSH EDPEVKFNWY VDGVEVHNAK TKPREEQYNS 300
TYRVVSVLTV LHQDWLNGKE YKCKVSNKAL PAPIEKTISK AKGQPREPQV YTLPPSREEM 360
TKNQVSLTCL VKGFYPSDIA VEWESNGQPE NNYKTTPPVL DSDGSFFLYS KLTVDKSRWQ 420
QGNVFSCSVM HEALHNHYTQ KSLSLSPGK                                  449
```

Amino acid sequence of the light chain of RGCLN18.2 antibody (SEQ ID NO: 34):

```
DIVMTQSPLS LPVTPGEPAS ISCKSSQSLL NSGNQKNYLT WYLQKPGQSP QLLIYWASTR  60
ESGVPDRFSG SGSGTDFTLK ISRVEAEDVG VYYCQNAYYY PYTFGGGTKV EIKRTVAAPS 120
VFIFPPSDEQ LKSGTASVVC LLNNFYPREA KVQWKVDNAL QSGNSQESVT EQDSKDSTYS 180
LSSTLTLSKA DYEKHKVYAC EVTHQGLSSP VTKSFNRGEC                      220
```

Example 6 Preparation of Antibody-Drug Conjugate (ADC)

The antibody-drug conjugate (ADC) was prepared using a common coupling method: a reducing agent and a protecting agent were prepared with purified water using 1-20 mM TCEP (tris-2-carboxyethyl-phosphine) and 1-20 mM DTPA (diethylene triamine pentacetate acid) stock solution. The reducing agent was mixed, at an amount varying within a certain concentration range according to the required coupling rate, with a certain concentration (e.g., 5-30 mg/mL) of a monoclonal antibody at a certain volume ratio (1:1) with stirring at 25° C. for 1 h of reaction, with a molar ratio of the final concentration of TCEP to the antibody being 0.5-6.0:1. The TCEP-reduced antibody may be used directly for conjugation.

A linker-active drug unit compound was prepared at a certain concentration (5 mM), dissolved in 25% DMSO (dimethyl sulfoxide), and slowly added with drug at a molar ratio of drug to thiol of 0.3-2.8:1, and stirred at 25° C. for 1-4 h of reaction. After the reaction was completed, centrifuga tion and ultrafiltration was performed 3 times with PBS buffer for purification to remove residual unreacted drugs and free small molecules such as DMSO. The conjugation was detected using SDS-PAGE electrophoresis and hydrophobic interaction chromatography-high performance liquid chromatography (HIC-HPLC).

The linker-active drug unit compounds used in this example were MC-Val-Cit-PAB-MMAE, D07-Val-Cit-PAB-MMAE and Py-MAA-Val-Cit-PAB-MMAE, which have the following structural formulas, respectively (refer to patent applications CN108853514A (page 14 of the specification), CN111433188A (page 53 of the specification), and WO2019223579A1 (pages 25-27 of the specification) for the synthesis methods).

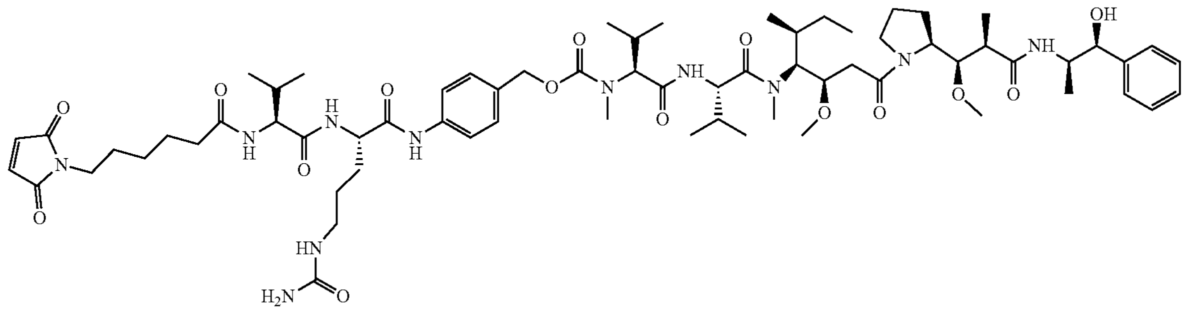

Mc-Val-Cit-PAB-MMAE

-continued
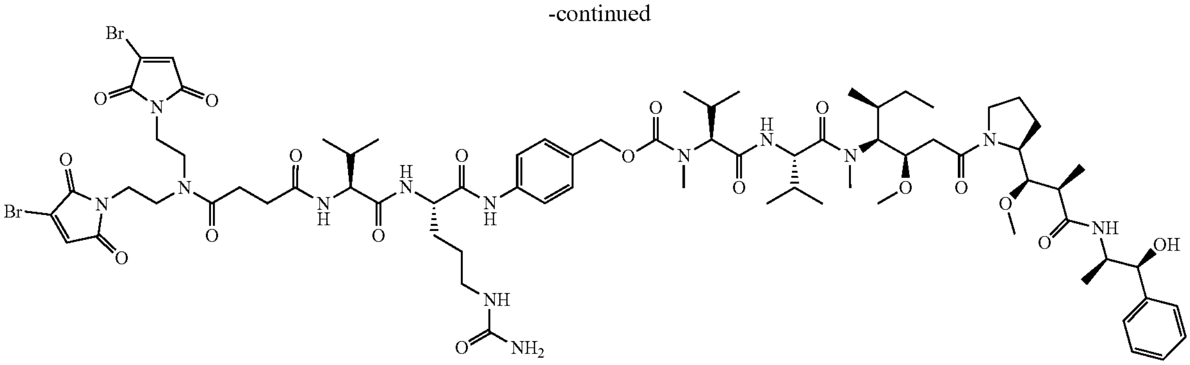
D07-Val-Cit-PAB-MMAE
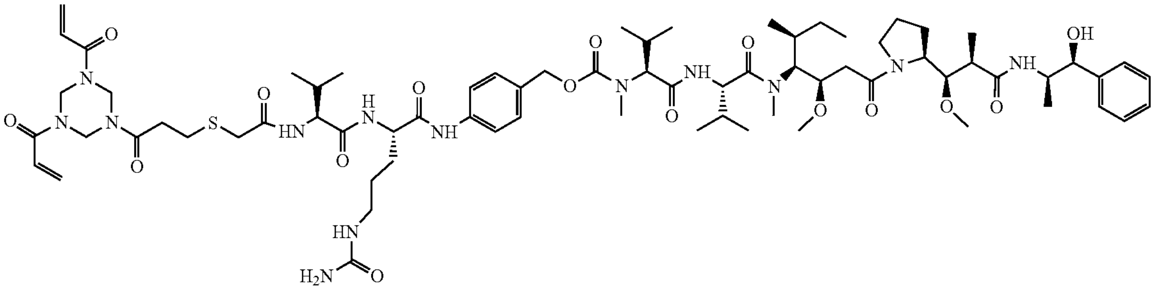
Py-MAA-Val-Cit-PAB-MMAE
The following ADCs were prepared by the above method (p is an integer selected from 1, 2, 3, 4, 5, 6, 7 and 8, q is an integer selected from 1, 2, 3 and 4, and Ab is the RGCLN18.2 antibody provided by the present disclosure), and the average DAR of these ADCs is 3.5-4.5.
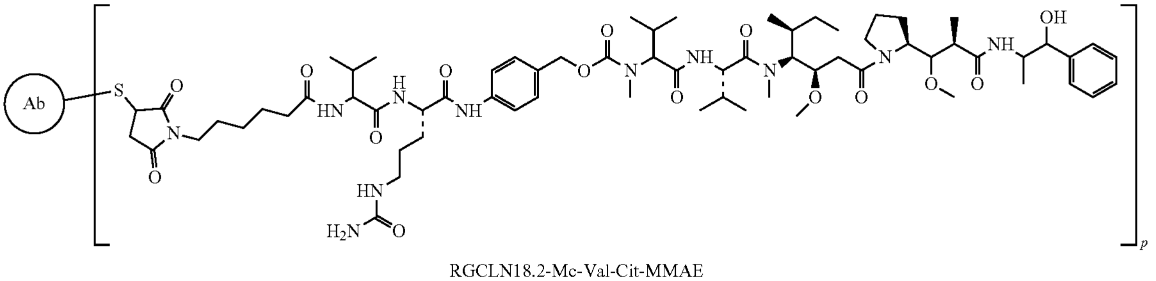
RGCLN18.2-Mc-Val-Cit-MMAE
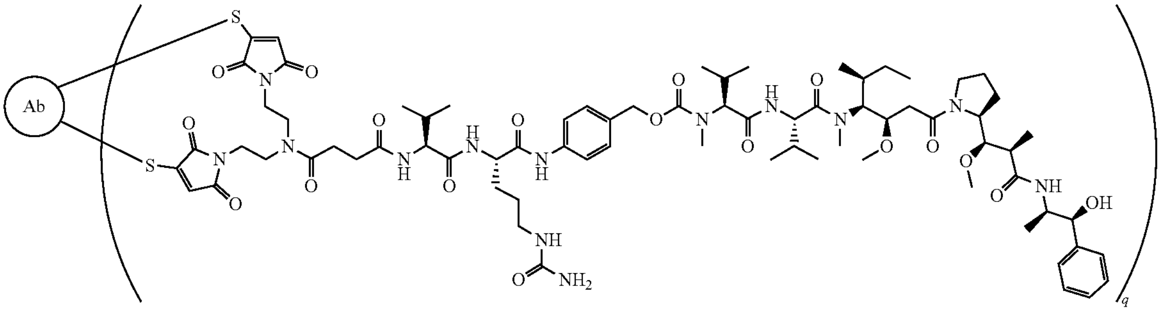
RGCLN18.2-D07-Val-Cit-PAB-MMAE -continued

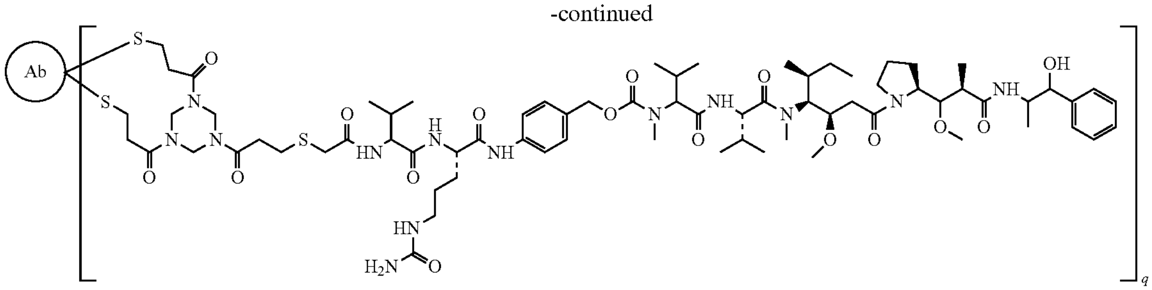

RGCLN18.2-PY-Val-Cit-MMAE and

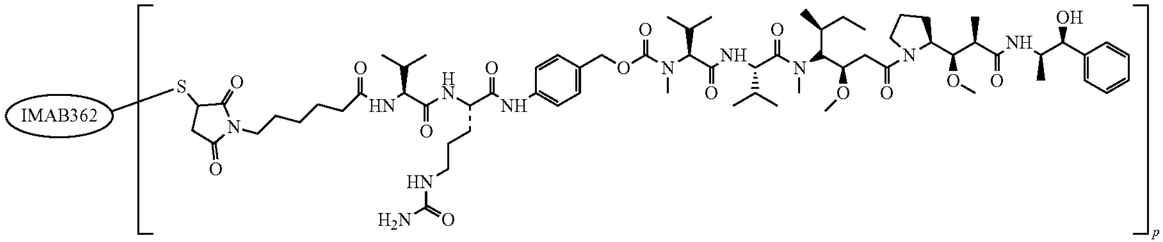

IMAB362-Mc-Val-Cit-MMAE

Example 7 Endocytosis Experiment of Antibody-Drug Conjugate

Figure 5:
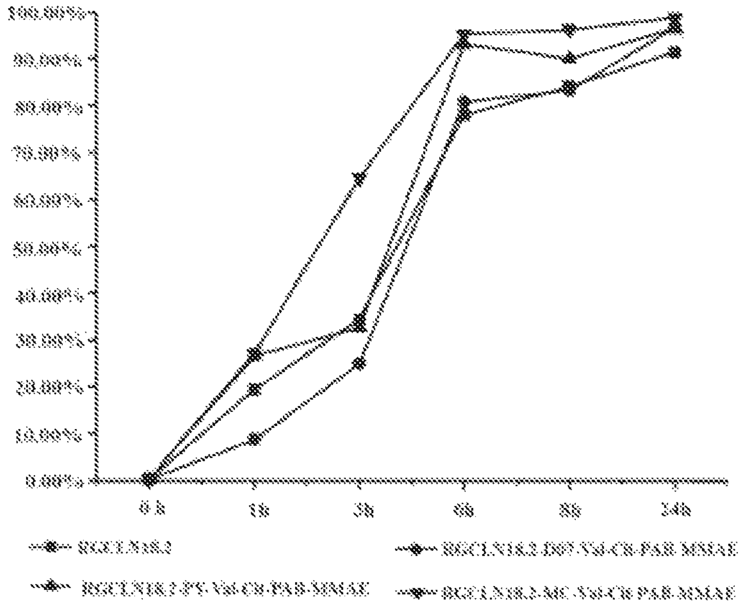
FIG. 5 is a graph showing the comparison of the endocytosis effect of RGCLN18.2, RGCLN18.2-PY-Val-Cit- PAB-MMAE, RGCLN18.2-MC-Val-Cit-PAB-MMAE, RGCLN18.2-D07-Val-Cit-PAB-MMAE and IMAB362-MC-Val-Cit-MMAE detected by flow cytometry.

The human gastric cancer cell line NCI-N87 cells were resuspended in the wells of a 6-well plate at approximately 1x10$^5$ cells per well. RGCLN18.2, RGCLN18.2-PY-Val-Cit-PAB-MMAE, RGCLN18.2-MC-Val-Cit-PAB-MMAE, and RGCLN18.2-D07-Val-Cit-PAB-MMAE were conjugated with pHAb amine reactive dye respectively, and then diluted to 10 μg/mL with cell culture medium. The cells were added with 100 μL of the dye complexes of RGCLN18.2 or ADCs, and incubated at 37° C. at an indicated time (0 h, 1 h, 3 h, 5 h, 21 h and 24 h). The endocytosis effect of RGCLN18.2 and ADCs was measured by a flow cytometer, and the results are shown in FIG. 5. From the results of the endocytosis experiment, it was found that the ADCs RGCLN18.2-PY-Val-Cit-PAB-MMAE, RGCLN18.2-MC-Val-Cit-PAB-MMAE, and RGCLN18.2-D07-Val-Cit-PAB-MMAE all had an endocytosis rate of about 98% at 24 h. The results show that the ADCs of RGCLN18.2 had a very good endocytosis effect in the human gastric cancer cell NCI-N87.

Example 8 In Vitro Cell Evaluation of Antibody-Drug Conjugate

The suspension of human gastric cancer cell line NCI-N87 cells was added to the wells of a 96-well plate at a density of 100 μL/well and 5000 cells/well, and then cultured overnight in a 37° C. water-saturated $CO_2$ incubator. The antibody-drug conjugates (RGCLN18.2-PY-Val-Cit-PAB-MMAE, RGCLN18.2-D07-Val-Cit-PAB-MMAE, RGCLN18.2-MC-Val-Cit-PAB-MMAE, IMAB362-MC-Val-Cit-MMAE) were serially diluted, added to the 96-well plate containing cells at 100 μL/well, and cultured for another 72 h in a 37° C. incubator. The OD value at 450 nm was read by a microplate reader, and the inhibition rate was calculated as IR %=(OD blank-OD drug)x100/OD blank. The $IC_{50}$ value was calculated by the curve fitting software Softmax Pro7.0.3 Gxp, and the results are shown in Table 7. From the above experimental data of the in vitro efficacy test, it was found that the ADCs RGCLN18.2-PY-Val-Cit-PAB-MMAE, RGCLN18.2-MC-Val-Cit-PAB-MMAE, and RGCLN18.2-D07-Val-Cit-PAB-MMAE had a better inhibition effect on proliferation than IMAB362-MC-Val-Cit-MMAE.

TABLE 7

In vitro IC50 value and maximum inhibition rate of antibody-drug conjugate

| ADC | DAR | $IC_{50}$ (ng/mL) | Inhibition rate (%) |
|---|---|---|---|
| RGCLN18 2-PY-Val-Cit-PAB-MMAE | 4.1 | 10.51 | 54.5 |
| RGCLN18.2-D07-Val-Cit-P AB-MMAE | 3.84 | 4.94 | 54.3 |
| RGCLN18.2-MC-Val-Cit-P AB-MMAE | 4.03 | 6.23 | 53.08 |
| IMAB362-MC-Val-Cit-P AB-MMAE | 4.22 | 501 | 52.27 |

Example 9 PDX (Patient-Derived Xenograft) Model Experiment of Antibody-Drug Conjugate The human pancreatic cancer tissue was washed, cut into small pieces, and inoculated on the right scapula of the back of nude mice with a trocar. When the tumor grew to 100-300 mm$^3$, the animals were randomly divided into groups. The administration of the control group and the experimental group is as shown in Table 8.

Table 8 Administration of control group and experimental group in PDX experiment

| Test drug | Number of dead animals |
|---|---|
| PBS | One died on Day 25 after administration |
| IMAB362-MC-Val-Cit-P AB-MMAE | One died each on Day 14, Day 18, and Day 53 |
| RGCLN18.2-MC-Val-Cit-P AB-MMAE | No death |

Figure 6:
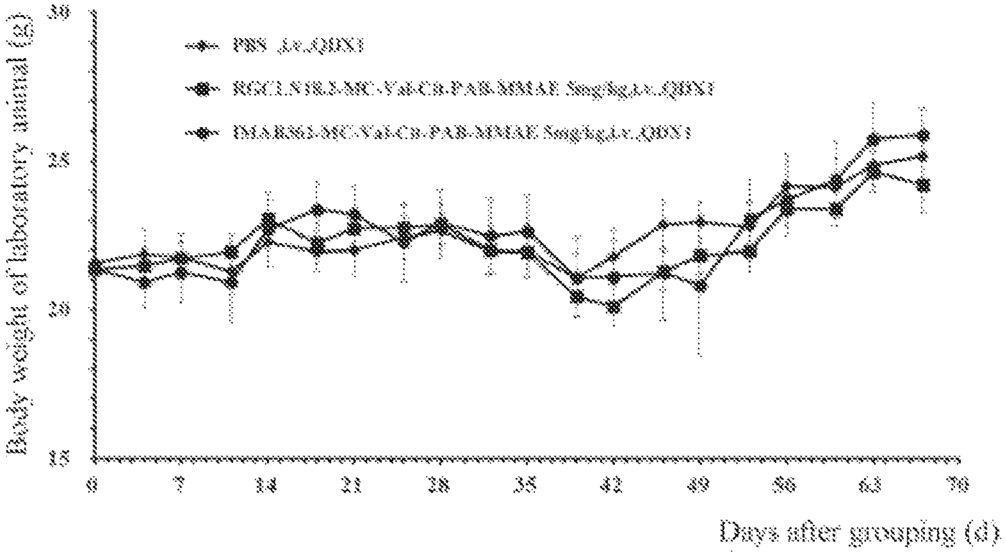
FIG. 6 is a graph showing the change in body weight of animals after administration of RGCLN18.2-MC-Val-Cit-PAB-MMAE, IMAB362-MC-Val-Cit-PAB-MMAE and PBS.
Figure 7:
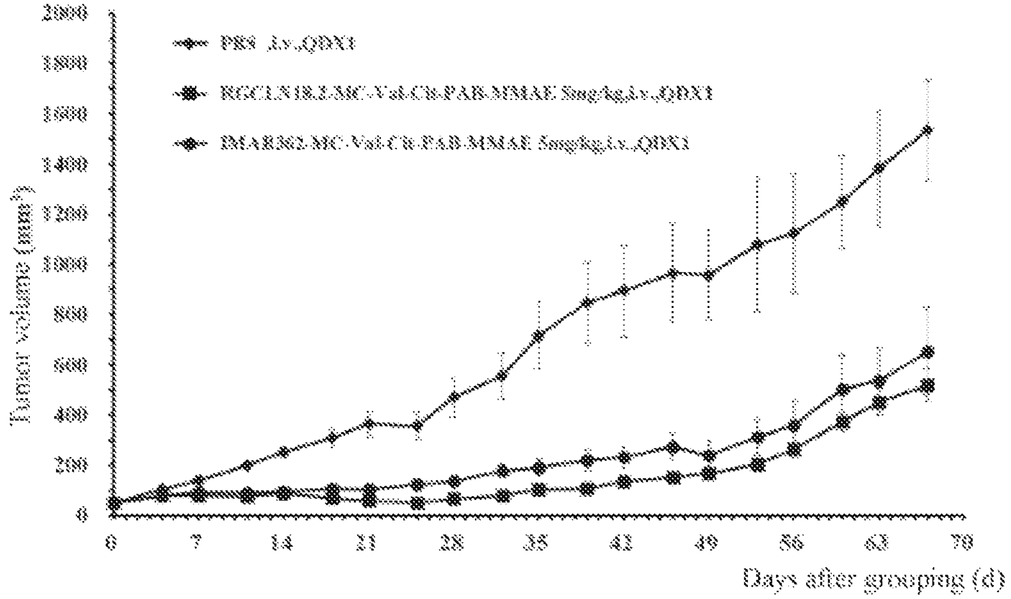
FIG. 7 is a graph showing the change in tumor volume of animals after administration of RGCLN18.2-MC-Val-Cit-PAB-MMAE, IMAB362-MC-Val-Cit-PAB-MMAE and PBS.

The experimental results are shown in FIG. 6 and FIG. 7, where FIG. 6 shows the graph of changes in the body weight of animals in the control group and the experimental group, and FIG. 7 shows the graph of changes in the tumor volume of animals in the control group and the experimental group. The results show that RGCLN18.2-MC-Val-Cit-PAB-MMAE had stronger anti-tumor effect than IMAB362-MC-Val-Cit-PAB-MMAE in human pancreatic cancer PDX model.

The above description is only for some embodiments by way of example only and without limitation to the combination of features necessary for carrying the present disclosure into effect. The headings provided herein are not intended to limit the various embodiments of the present disclosure. Terms such as "including", "comprising" and "containing" are not intended to be limiting. In addition, unless otherwise indicated, the singular form "a", "an", or "the" includes plural references, as well as "or" means "and/or". Unless otherwise defined herein, all technical and scientific terms used herein have the same meaning as commonly understood in the art.

All publications and patents mentioned in the present application are incorporated herein by reference. Without departing from the scope and spirit of the present disclosure, various modifications and variations of the described method and composition of the present disclosure will be apparent. Although the present disclosure has been described by using embodiments, it should be understood that the disclosure should not be unduly limited to these embodiments.

The invention claimed is:

1. An anti-Claudin 18.2 antibody or antigen-binding fragment thereof, comprising a heavy chain variable region and a light chain variable region, wherein the heavy chain variable region and the light chain variable region have CDRs sequences identical to that of an antibody defined by the following sequences or obtained by 1-2 amino acid substitutions of the CDRs of the antibody defined by the following sequences:

(1) an amino acid sequence of a heavy chain variable region as shown in SEQ ID NO: 1; and (2) an amino acid sequence of a light chain variable region as shown in SEQ ID NO: 2.

2. The antibody or antigen-binding fragment thereof according to claim 1, wherein:

(1) for the heavy chain variable region, CDR1 has an amino acid sequence as shown in SEQ ID NO: 3, 4, 5, 6 or 7 or obtained by 1 or 2 amino acid substitutions of SEQ ID NO: 3, 4, 5, 6 or 7; CDR2 has an amino acid sequence as shown in SEQ ID NO: 8, 9, 10, 11 or 12, or obtained by 1 or 2 amino acid substitutions of SEQ ID NO: 8, 9, 10, 11 or 12; and CDR3 has an amino acid sequence as shown in SEQ ID NO: 13, 14, 15, 16 or 17, or obtained by 1 or 2 amino acid substitutions of SEQ ID NO: 13, 14, 15, 16 or 17; and (2) for the light chain variable region, CDR1 has an amino acid sequence as shown in SEQ ID NO: 18, 19, 20, 21 or 22 or obtained by 1 or 2 amino acid substitutions of SEQ ID NO: 18, 19, 20, 21 or 22; CDR2 has an amino acid sequence as shown in SEQ ID NO: 23, 24, 25, 26 or 27, or obtained by 1 or 2 amino acid substitutions of SEQ ID NO: 23, 24, 25, 26 or 27; and CDR3 has an amino acid sequence as shown in SEQ ID NO: 28, 29, 30, 31 or 32, or obtained by 1 or 2 amino acid substitutions of SEQ ID NO: 28, 29, 30, 31 or 32.

3. The antibody or antigen-binding fragment thereof according to claim 2, wherein, (1) CDRs 1-3 of the heavy chain variable region have amino acid sequences of SEQ ID NOs: 3, 8 and 13 or obtained by 1 or 2 amino acid substitutions of SEQ ID NOs: 3, 8 and 13, and the CDRs 1-3 of the light chain variable region have amino acid sequences of SEQ ID NOs: 18, 23 and 28 or obtained by 1 or 2 amino acid substitutions of SEQ ID NOs: 18, 23 and 28;

(2) CDRs 1-3 of the heavy chain variable region have amino acid sequences of SEQ ID NOs: 4, 9 and 14 or obtained by 1 or 2 amino acid substitutions of SEQ ID NOs: 4, 9 and 14, and the CDRs 1-3 of the light chain variable region have amino acid sequences of SEQ ID NOs: 19, 24 and 29 or obtained by 1 or 2 amino acid substitutions of SEQ ID NOs: 19, 24 and 29;

(3) CDRs 1-3 of the heavy chain variable region have amino acid sequences of SEQ ID NOs: 5, 10 and 15 or obtained by 1 or 2 amino acid substitutions of SEQ ID NOs: 5, 10 and 15, and the CDRs 1-3 of the light chain variable region have amino acid sequences of SEQ ID NOs: 20, 25 and 30 or obtained by 1 or 2 amino acid substitutions of SEQ ID NOs: 20, 25 and 30;

(4) CDRs 1-3 of the heavy chain variable region have amino acid sequences of SEQ ID NOs: 6, 11 and 16 or obtained by 1 or 2 amino acid substitutions of SEQ ID NOs: 6, 11 and 16, and the CDRs 1-3 of the light chain variable region have amino acid sequences of SEQ ID NOs: 21, 26 and 31 or obtained by 1 or 2 amino acid substitutions of SEQ ID NOs: 21, 26 and 31; or (5) CDRs 1-3 of the heavy chain variable region have amino acid sequences of SEQ ID NOs: 7, 12 and 17 or obtained by 1 or 2 amino acid substitutions of SEQ ID NOs: 7, 12 and 17, and the CDRs 1-3 of the light chain variable region have amino acid sequences of SEQ ID NOs: 22, 27 and 32 or obtained by 1 or 2 amino acid substitutions of SEQ ID NOs: 22, 27 and 32.

4. The antibody or antigen-binding fragment thereof according to claim 1, wherein:

(1) the heavy chain variable region has an amino acid sequence as shown in SEQ ID NO:

1, or comprises the same CDRs 1-3 as in SEQ ID NO: 1 and has an amino acid sequence having more than 80%, 85%, 90%, 95%, 96%, 97%, 98%, or 99% identical to SEQ ID NO: 1; and (2) the light chain variable region has an amino acid sequence as shown in SEQ ID NO: 2, or comprises the same CDRs 1-3 as in SEQ ID NO: 2 and has an amino acid sequence having more than 80%, 85%, 90%, 95%, 96%, 97%, 98%, or 99% identical to SEQ ID NO: 2;

or (3) the heavy chain has an amino acid sequence as shown in SEQ ID NO: 33; and (2) (4) the light chain has an amino acid sequence as shown in SEQ ID NO: 34.

5. The antibody or antigen-binding fragment thereof according to claim 1, wherein the antibody or antigen-binding fragment thereof includes a monoclonal antibody, Fab, Fab', Fab'-SH, $F(ab')_2$, Fv, single chain Fv (scFv), bispecific antibody, multispecific antibody, chimeric antibody, humanized antibody or fusion protein comprising an antigen-binding fragment of an antibody.

6. The antibody or antigen-binding fragment thereof according to claim 1, further comprising a human or murine constant region.

7. An antibody-drug conjugate comprising the antibody or antigen-binding fragment thereof according to claim 1.

8. The antibody-drug conjugate according to claim 7, wherein the antibody-drug conjugate has a structure represented by formula (I):

Ab-L-D (I)

wherein:

Ab is the antibody or antigen-binding fragment thereof according to claim 1;

D is an active drug unit;

L is any linking group, which is covalently linked to the antibody or antigen-binding fragment thereof Ab and the active drug unit D, respectively;

wherein, Ab is linked to one or more active drug units D through one or more linking groups L.

9. The antibody-drug conjugate according to claim 8, wherein L is covalently linked to an amino residue or a thiol residue of the antibody Ab.

10. The antibody-drug conjugate according to claim 8, wherein L includes a cleavable linker and a non-cleavable linker.

11. The antibody-drug conjugate according to claim 8, wherein L comprises a structure selected from the group consisting of:

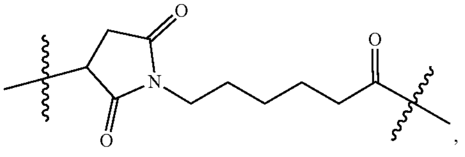
,
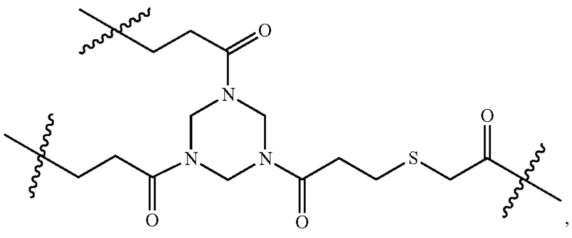
,
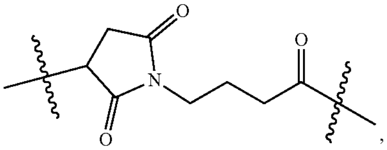
,
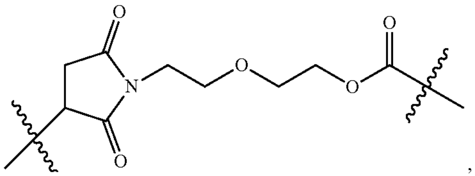
,
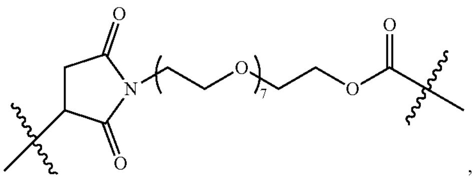
,
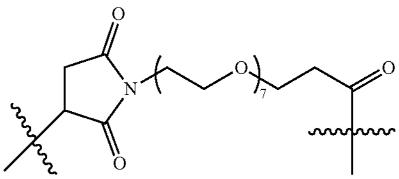
,
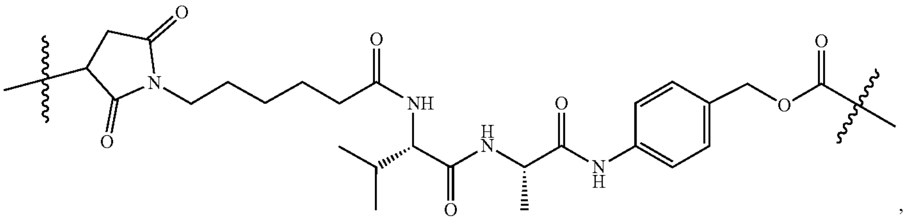
,
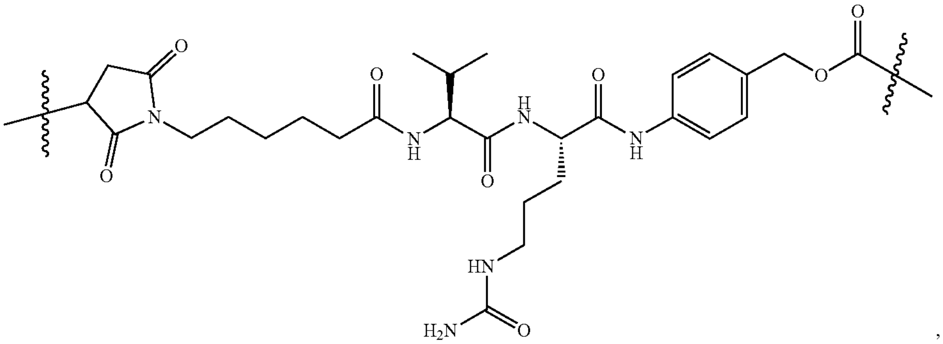
,
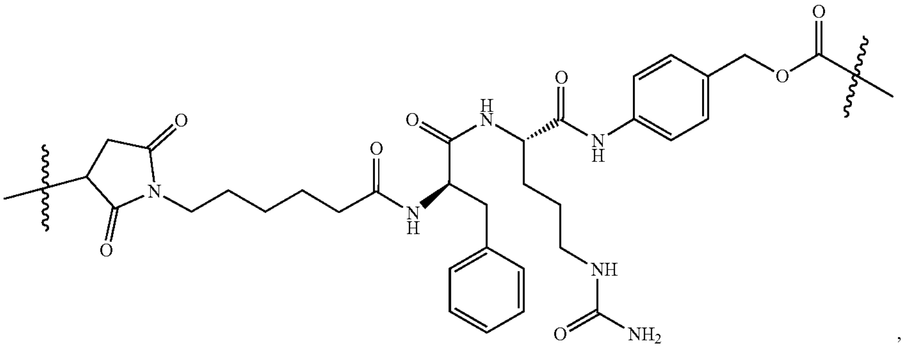
, -continued
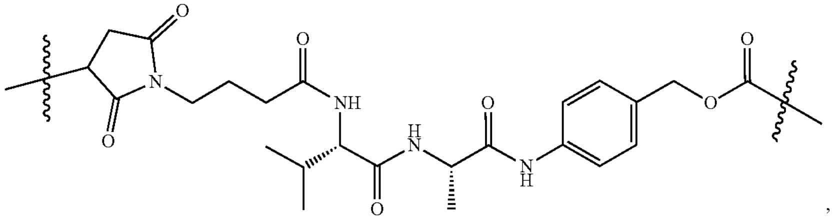
,
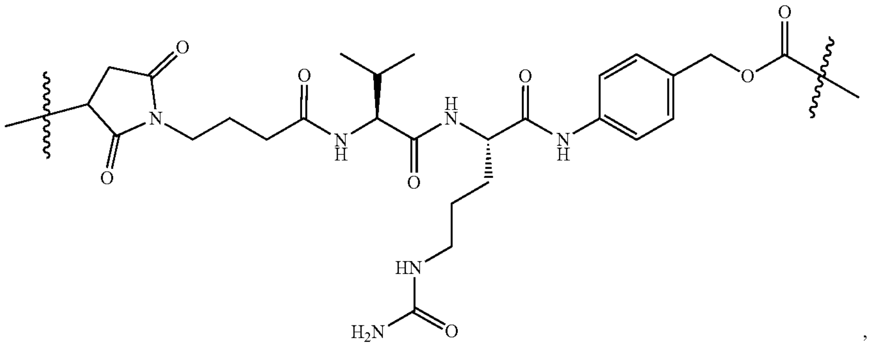
,
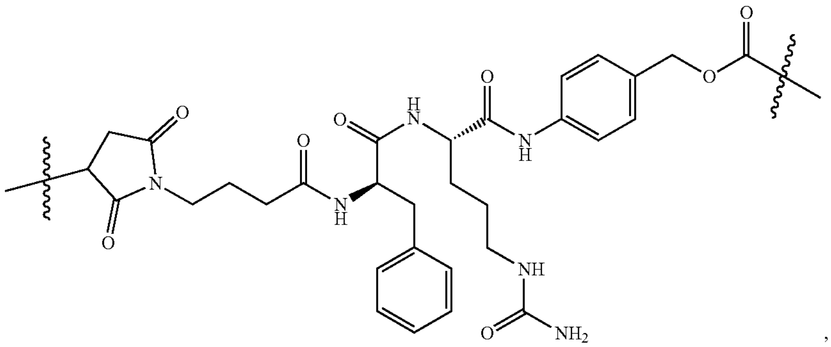
,
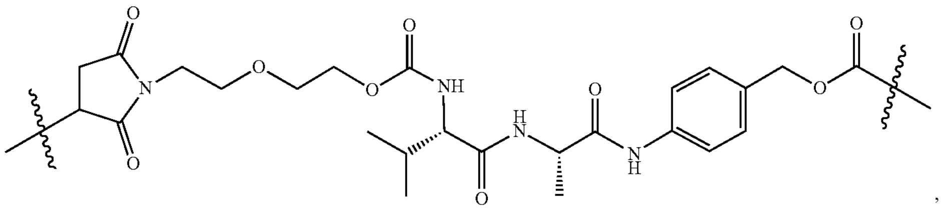
,
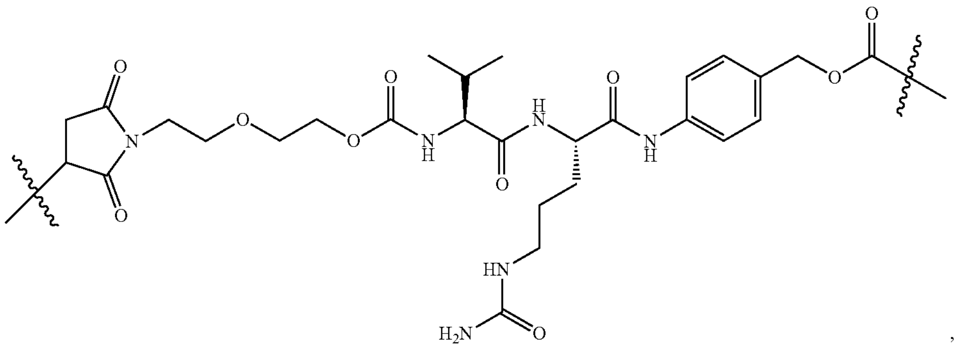
, -continued
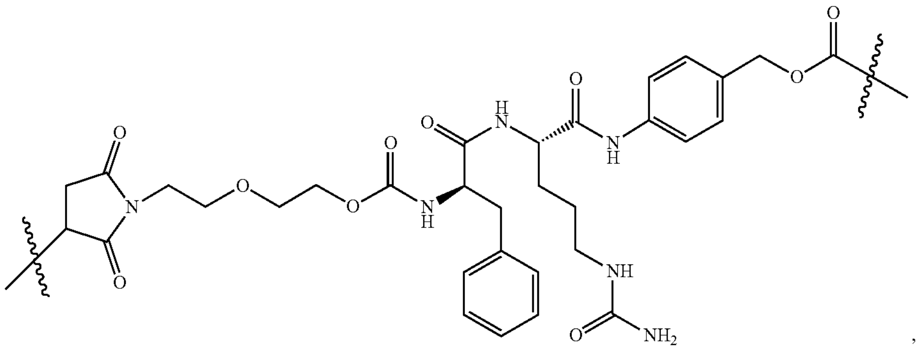
,
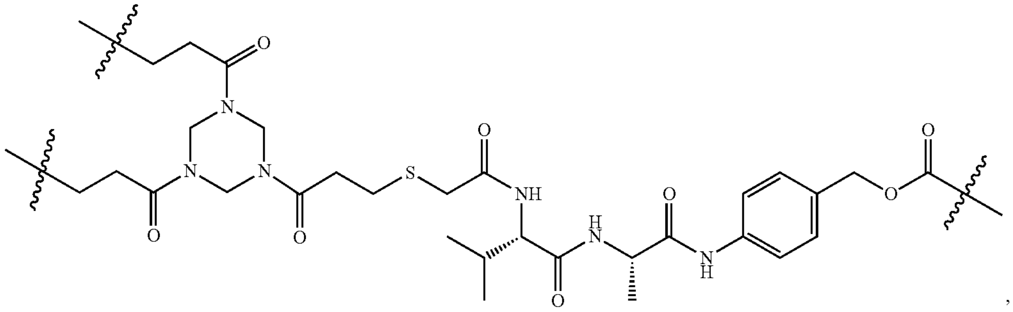
,
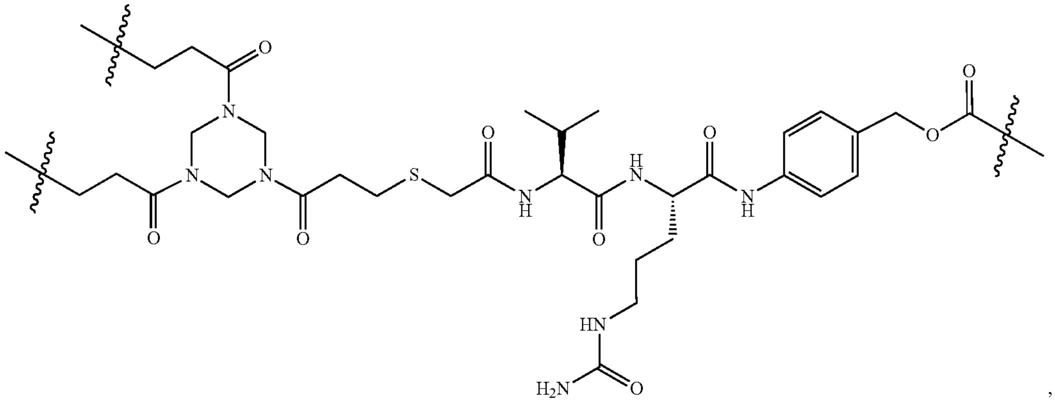
,
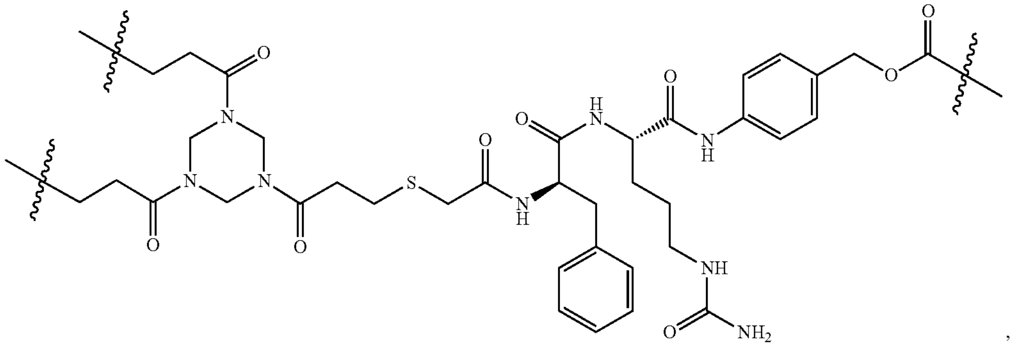
,
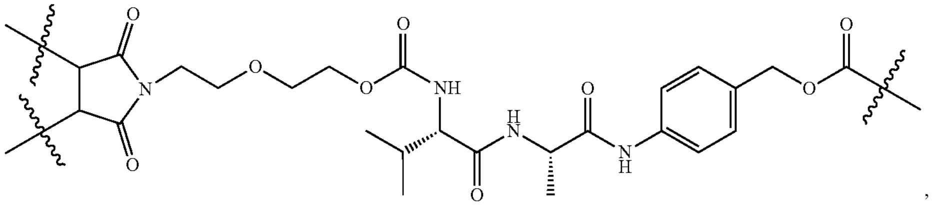
, -continued
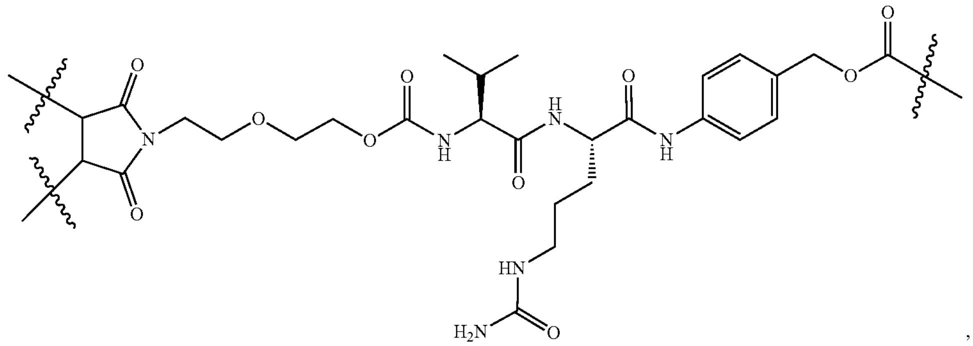
,
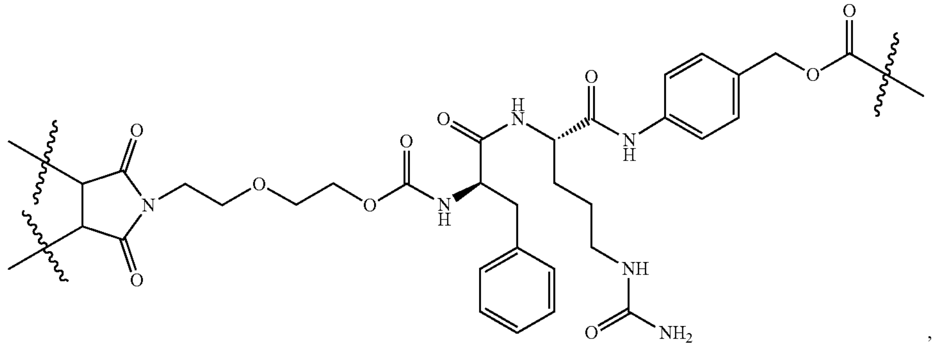
,
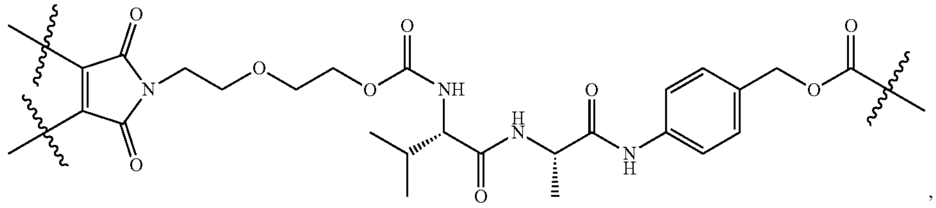
,
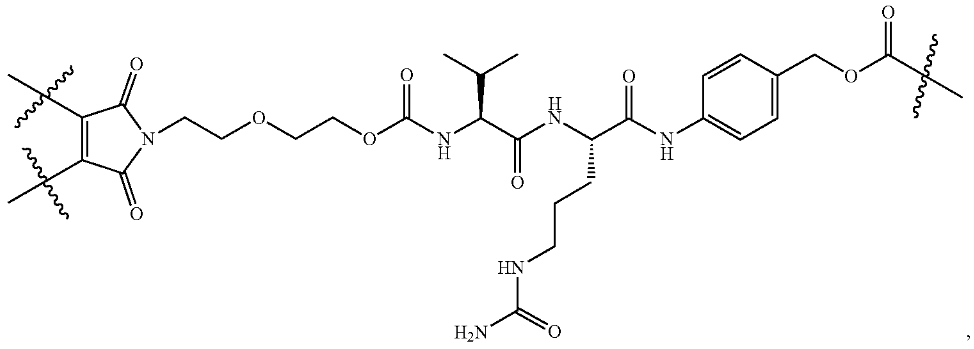
,
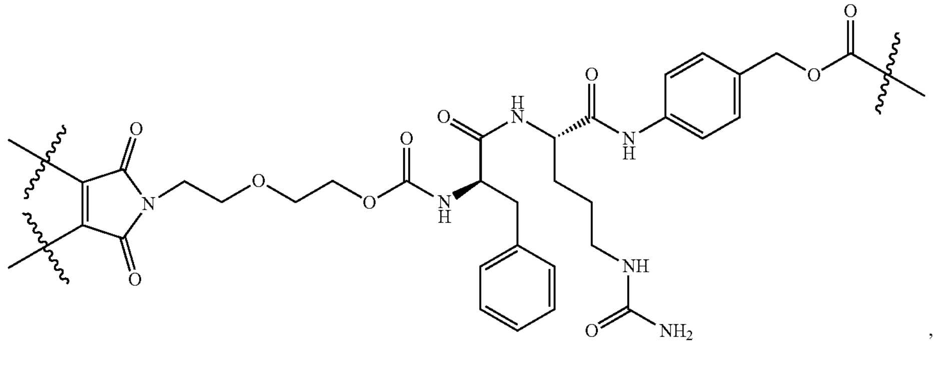
, -continued
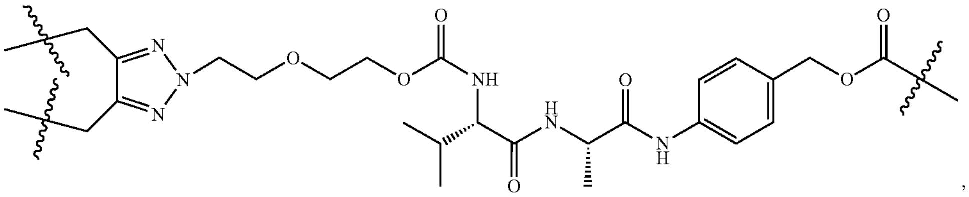
,
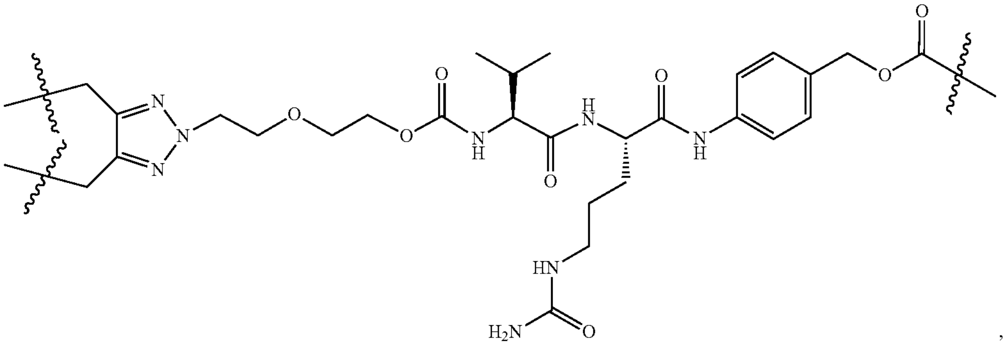
,
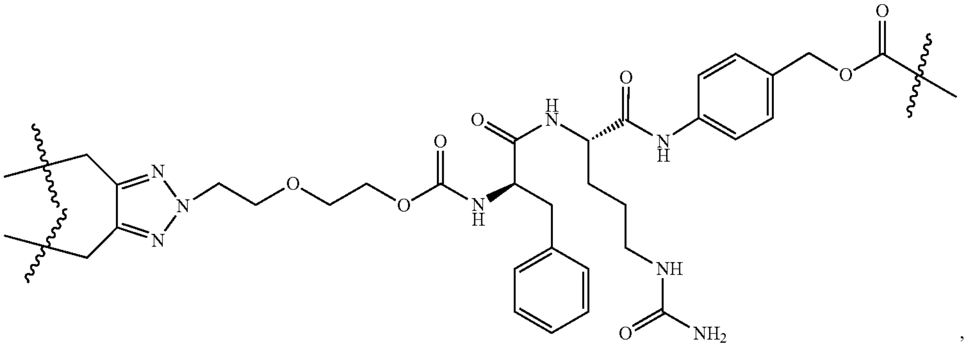
,
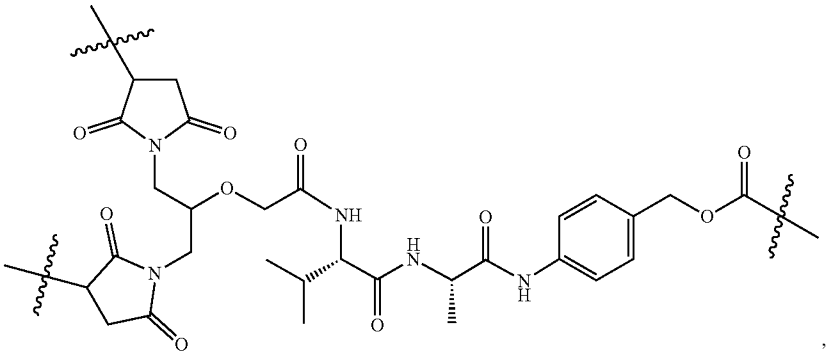
,
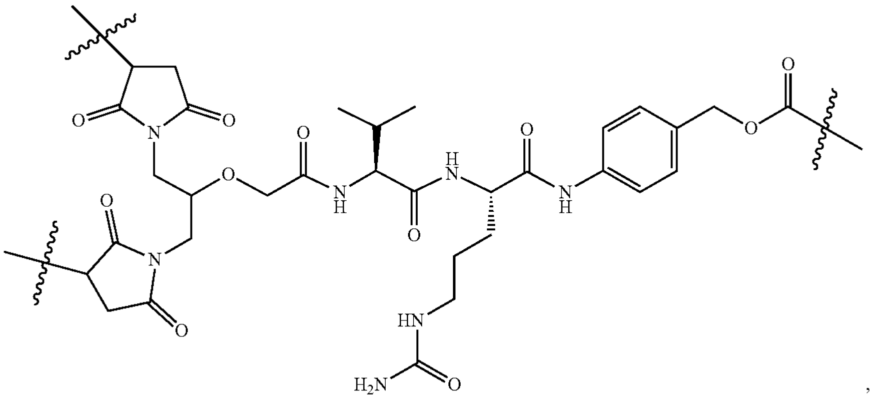
, -continued
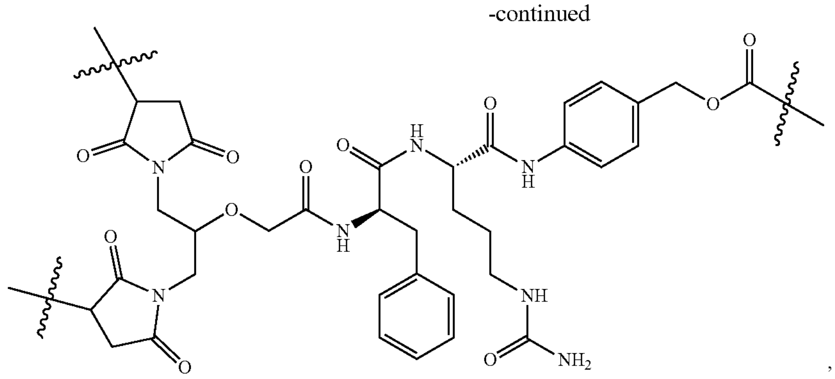
,
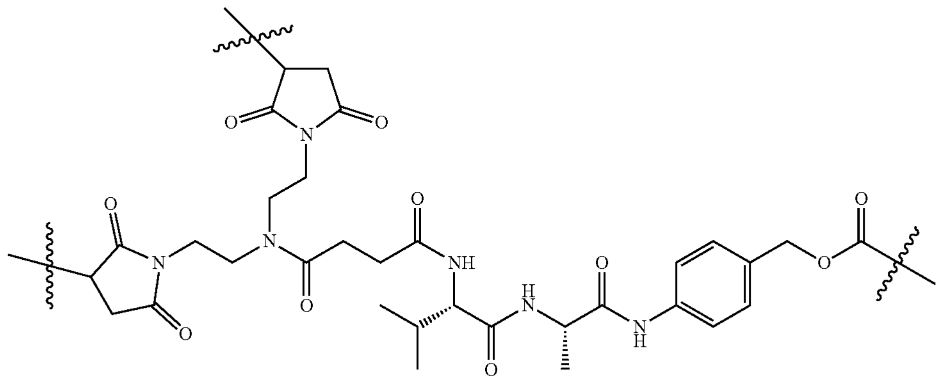
,
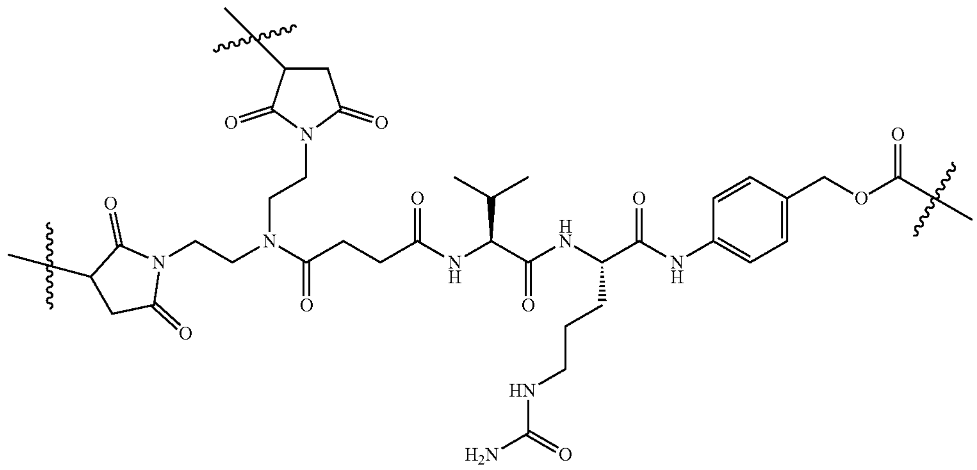
,
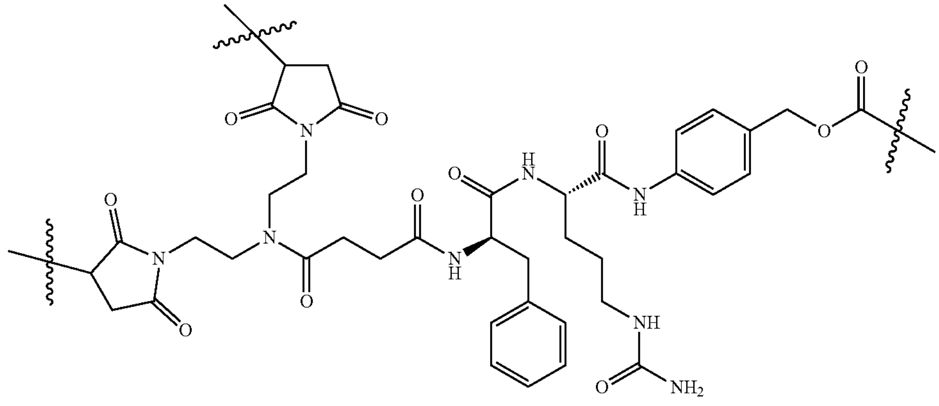
, -continued

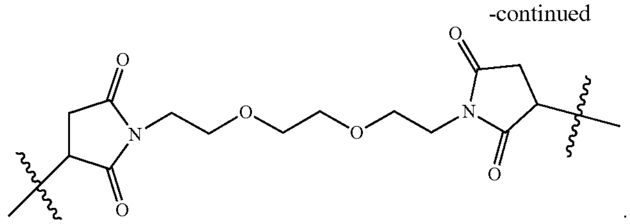

.

12. The antibody-drug conjugate according to claim 8, wherein the active drug unit D is selected from the group consisting of a cytotoxic molecule, cell differentiation factor, stem cell trophic factor, steroid drug, drug for the treatment of autoimmune diseases, anti-inflammatory drug, and drug for the treatment of infectious diseases.

13. The antibody-drug conjugate according to claim 8, wherein the active drug unit D has a structure selected from the group consisting of:

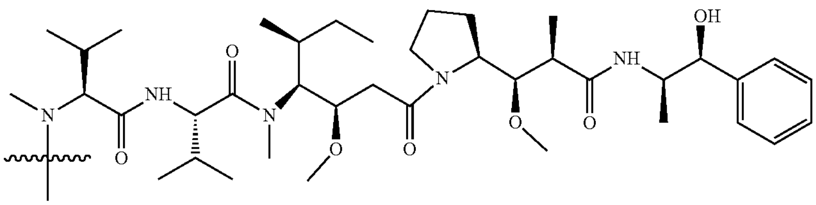

,

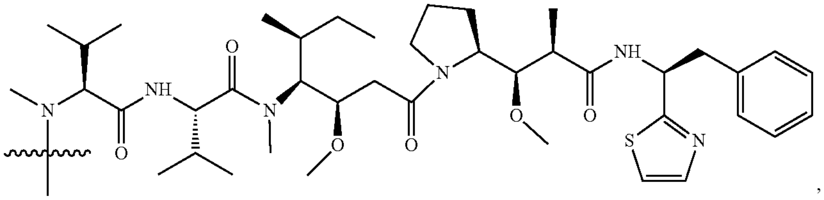

,

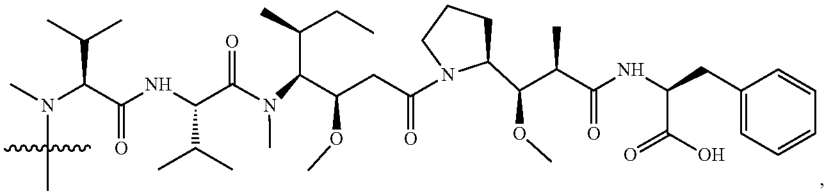

,

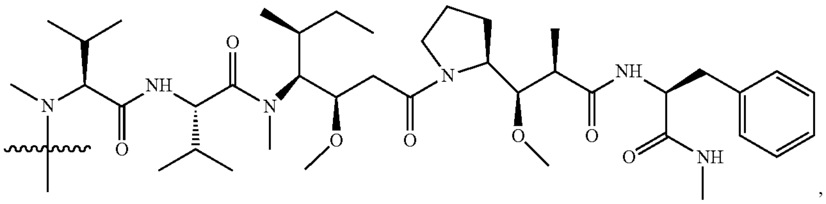

,

-continued
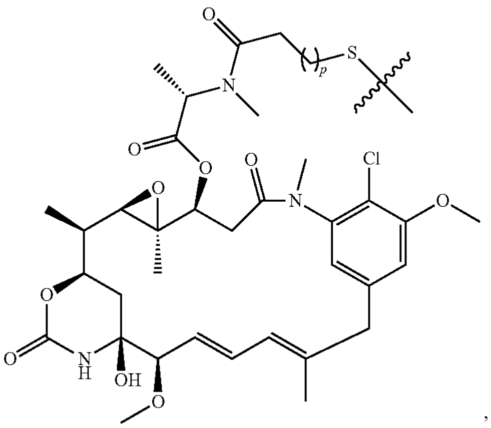
,
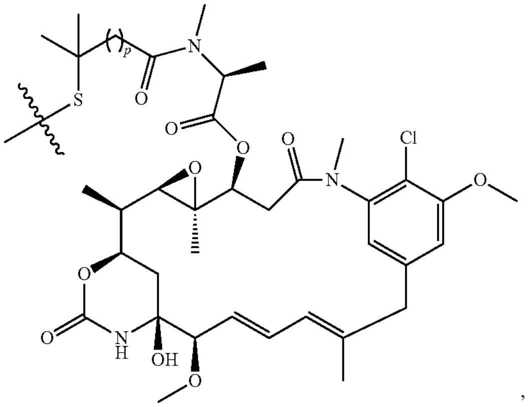
,
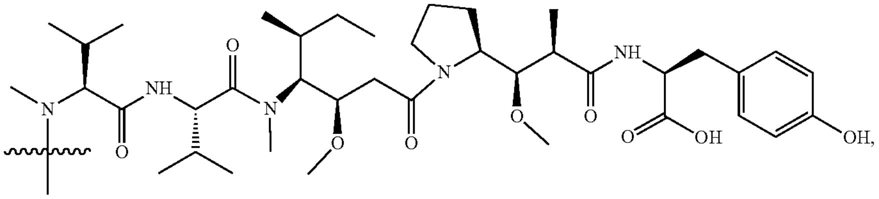
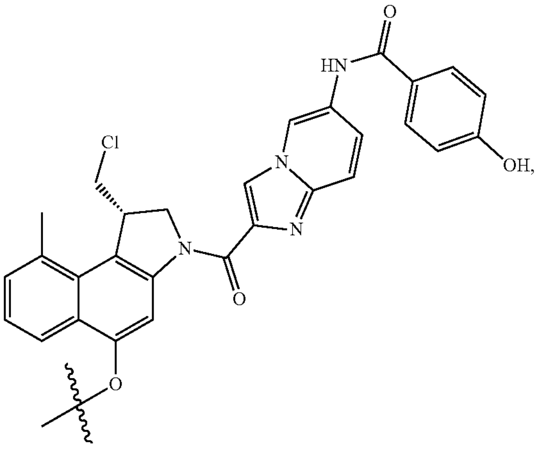

-continued
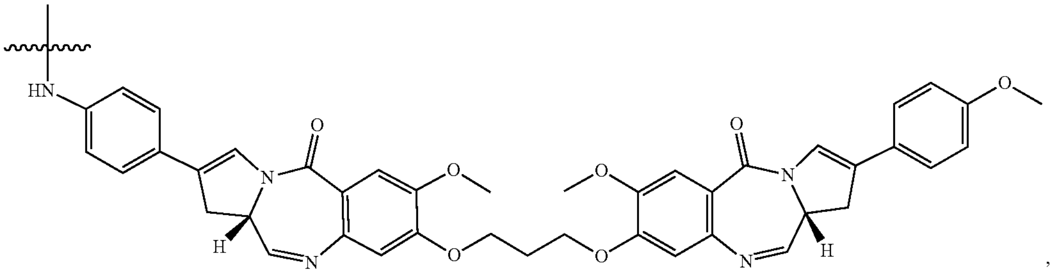
,
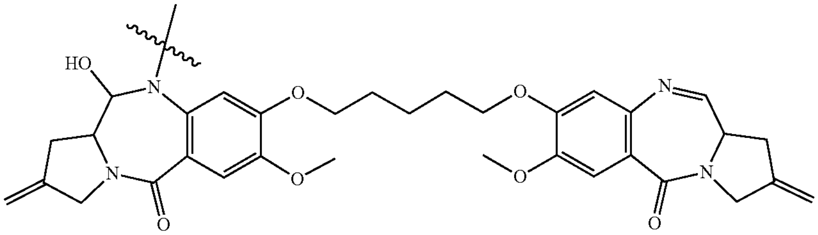
,
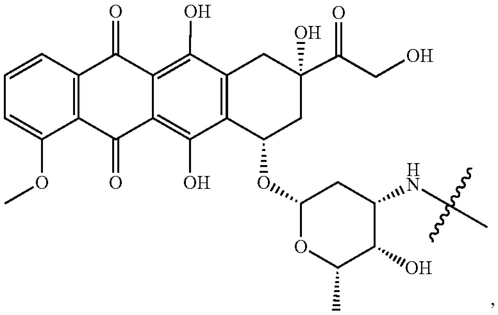
,
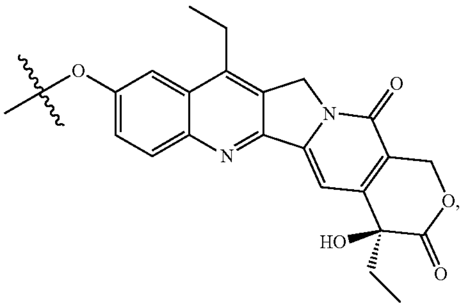
,
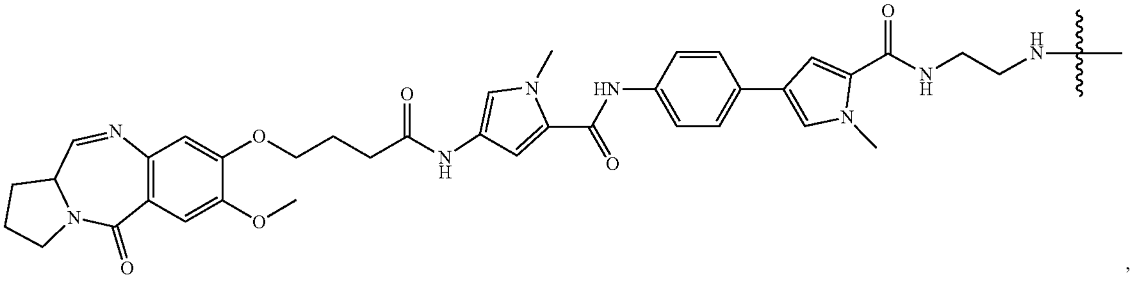
,
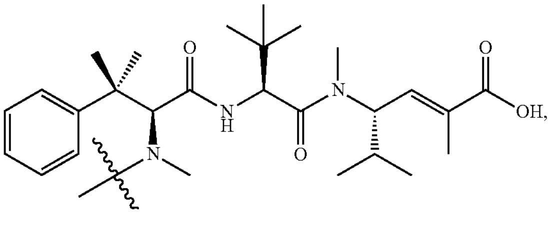
, -continued
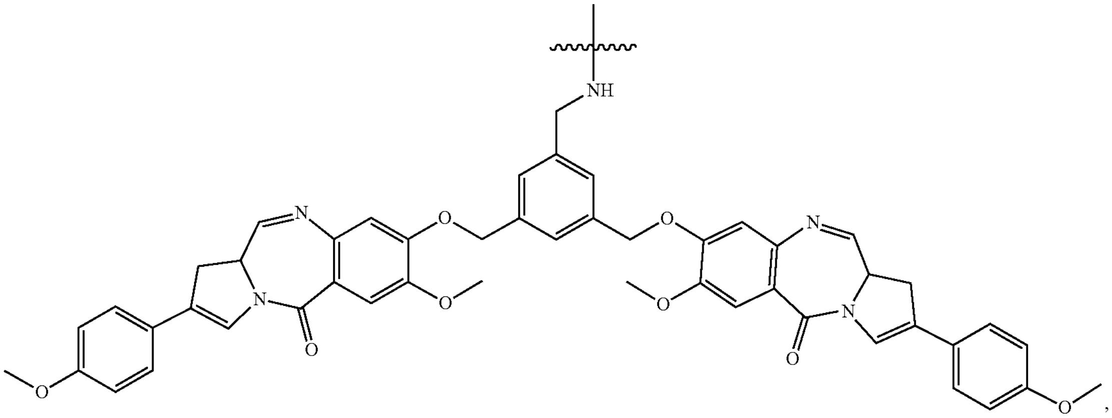
,
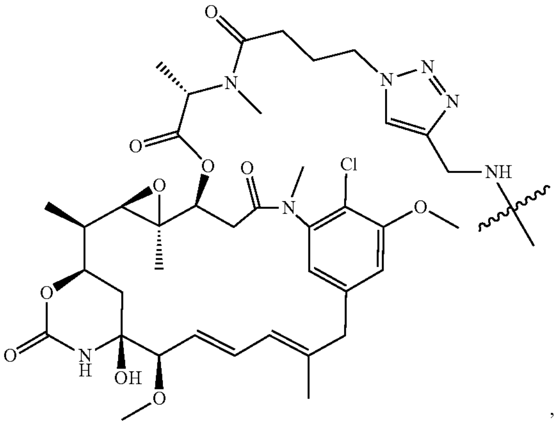
,
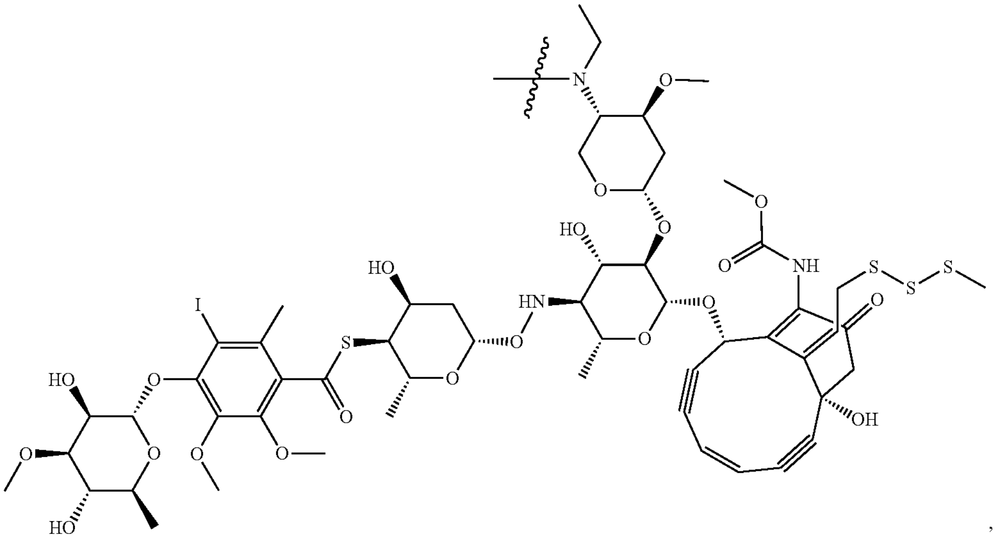
,
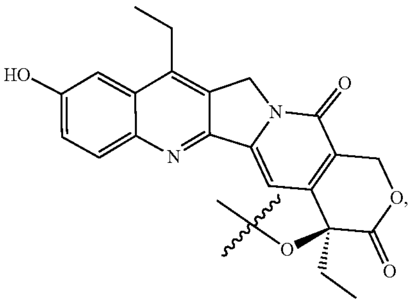
, -continued
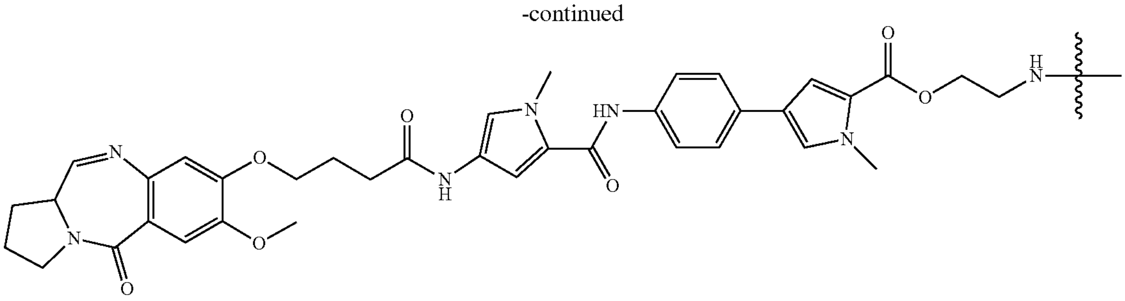
,
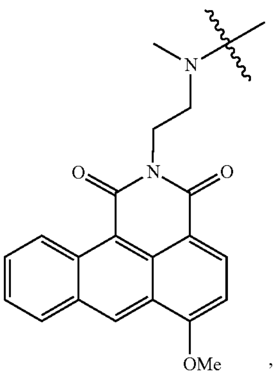
,
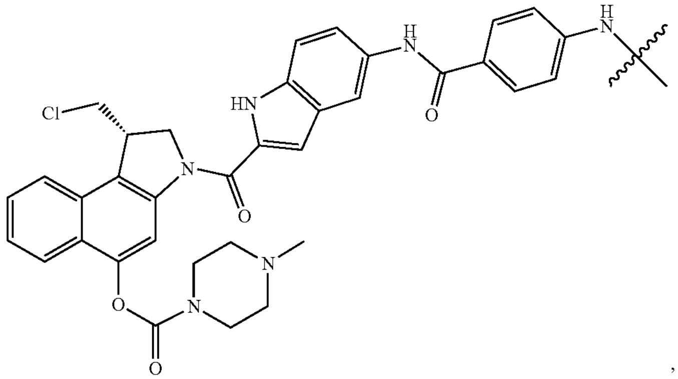
,
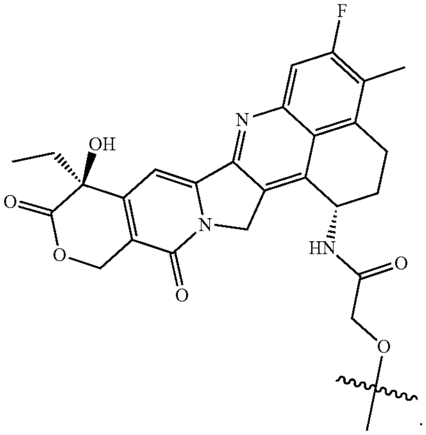
.
14. The antibody-drug conjugate according to claim 8, wherein the antibody-drug conjugate has a structure selected from the group consisting of:
ADC-1
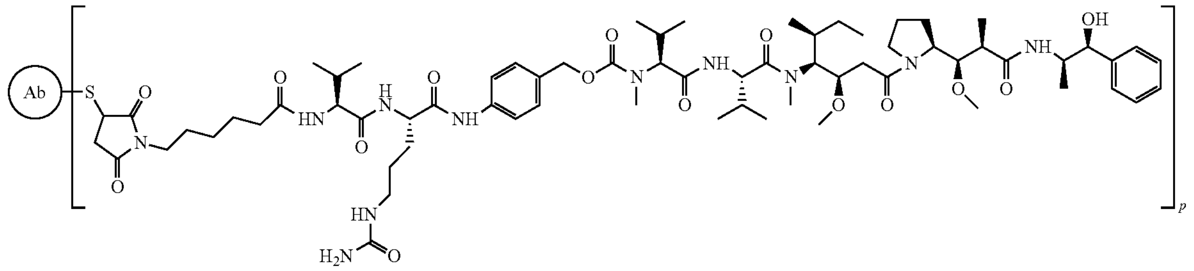

-continued

ADC-2

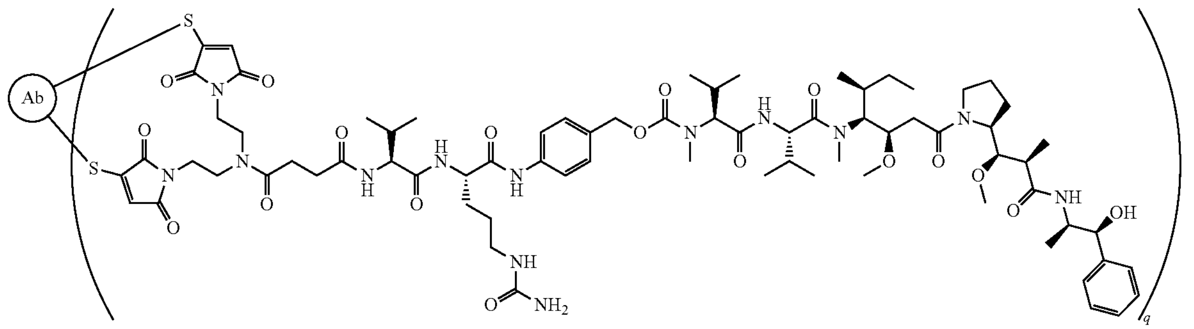

ADC-3

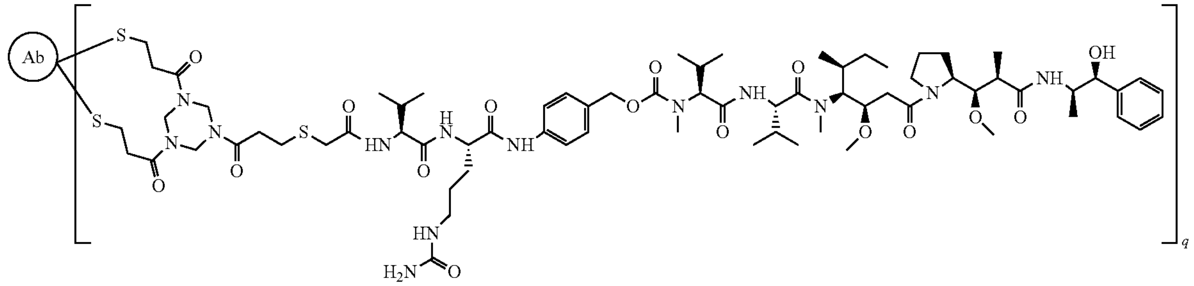

wherein, p is an integer selected from 1, 2, 3, 4, 5, 6, 7, and 8, and q is an integer selected from 1, 2, 3, and 4.

15. An isolated polynucleotide or combination thereof, encoding the antibody or antigen-binding fragment thereof according to claim 1.

16. A nucleic acid construct comprising the polynucleotide according to claim 15.

17. A host cell comprising the nucleic acid construct according to claim 16.

18. A pharmaceutical composition comprising the antibody or antigen-binding fragment thereof according to claim 1, and a pharmaceutically acceptable carrier.

19. A method for producing an anti-Claudin 18.2 antibody, comprising culturing the host cell according to claim 17 under a condition suitable for expressing a vector encoding an anti-Claudin 18.2 antibody or an antigen-binding fragment thereof, and recovering the antibody or fragment.

20. A method for treating cancer, comprising administering the antibody or antigen-binding fragment thereof according to claim 1 to a subject in need thereof.

21. The antibody or antigen-binding fragment thereof according to claim 5, wherein the antibody is a humanized monoclonal antibody.

22. The antibody or antigen-binding fragment thereof according to claim 6, wherein the constant region is selected from the group consisting of IgG1, IgG2, IgG3, and IgG4.

23. The antibody-drug conjugate according to claim 9, wherein L is covalently linked to a thiol residue formed by breaking an interchain disulfide bond of the antibody Ab.

24. The antibody-drug conjugate according to claim 10, wherein the cleavable linker includes a peptide unit comprising 2 to 20 amino acids.

25. The antibody-drug conjugate according to claim 24, wherein the peptide unit is selected from the group consisting of-valine-citrulline-(-Val-Cit-),-glycine-glycine-phenylalanine-glycine-(-Gly-Gly-Phe-Gly-),-valine-alanine-(-Val-Ala-),-valine-lysine-(-Val-Lys-),-valine-arginine-(-Val-Arg-),-phenylalanine- citrulline-(-Phe-Cit-),-phenylalanine-lysine-(-Phe-Lys-),-phenylalanine-arginine-(-Phe-Arg-) and a combination thereof.

26. The antibody-drug conjugate according to claim 12, wherein the cytotoxic molecule is selected from the group consisting of a tubulin inhibitor or a DNA damaging agent.

27. The antibody-drug conjugate according to claim 26, wherein the tubulin inhibitor is selected from the group consisting of a cytotoxic molecule of dolastatins and auristatins, a cytotoxic molecule of maytansines; the DNA damaging agent is selected from the group consisting of calicheamicins, duocarmycins, anthramycin derivative pyrrolobenzodiazepine (PBD), camptothecins and a derivative thereof, and SN-38.

28. The antibody-drug conjugate according to claim 27, wherein the cytokine molecule of auristatins is selected from the group consisting of MMAE, MMAF, or a derivative thereof; and the cytotoxic molecule of maytansines is selected from the group consisting of DM1, DM4, or a derivative thereof.

29. The nucleic acid construct according to claim 16, wherein the nucleic acid construct is a vector.

30. The host cell according to claim 17, wherein the cell is selected from the group consisting of a prokaryotic cell, eukaryotic cell, yeast cell, mammalian cell, *E. coli* cell or CHO cell, NS0 cell, Sp2/0 cell, and BHK cell.

31. The method according to claim 20, wherein the cancer is a solid tumor.

32. The method according to claim 31, wherein the solid tumor is selected from the group consisting of gastric cancer and pancreatic cancer.

* * * * *